US009002497B2

(12) United States Patent
Volk et al.

(10) Patent No.: US 9,002,497 B2
(45) Date of Patent: Apr. 7, 2015

(54) METHODS AND SYSTEMS FOR INSPECTION OF WAFERS AND RETICLES USING DESIGNER INTENT DATA

(75) Inventors: William Volk, San Francisco, CA (US); James Wiley, Menlo Park, CA (US); Sterling Watson, Palo Alto, CA (US); Sagar A. Kekare, Plano, TX (US); Carl Hess, Los Altos, CA (US); Paul Frank Marella, San Jose, CA (US); Sharon McCauley, San Jose, CA (US); Ellis Chang, Saratoga, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 1486 days.

(21) Appl. No.: 10/883,372

(22) Filed: Jul. 1, 2004

(65) Prior Publication Data

US 2005/0004774 A1    Jan. 6, 2005

Related U.S. Application Data

(60) Provisional application No. 60/485,338, filed on Jul. 3, 2003.

(51) Int. Cl.
*G06F 19/00* (2011.01)
*G03F 1/84* (2012.01)
(Continued)

(52) U.S. Cl.
CPC .............. *G03F 1/84* (2013.01); *G01N 21/9501* (2013.01); *G01N 21/956* (2013.01); *G03F 7/7065* (2013.01); *G01N 2021/95676* (2013.01)

(58) Field of Classification Search
USPC ............ 700/121, 182, 98; 382/144, 149, 145, 382/202; 703/45, 14; 438/14; 356/237.23
See application file for complete search history.

(56) References Cited

U.S. PATENT DOCUMENTS 5,023,424 A   6/1991   Vaught
5,971,586 A   10/1999  Mori
(Continued)

FOREIGN PATENT DOCUMENTS

CN   1316101      10/2001
JP   Hei 5-13256   2/1993
(Continued)

OTHER PUBLICATIONS

Synopsys Products—Virtual Stepper, © 2003, pp. 1-5.
(Continued)

*Primary Examiner* — Kidest Bahta
(74) *Attorney, Agent, or Firm* — Ann Marie Mewherter

(57) ABSTRACT

Methods and systems for inspection of wafers and reticles using designer intent data are provided. One computer-implemented method includes identifying nuisance defects on a wafer based on inspection data produced by inspection of a reticle, which is used to form a pattern on the wafer prior to inspection of the wafer. Another computer-implemented method includes detecting defects on a wafer by analyzing data generated by inspection of the wafer in combination with data representative of a reticle, which includes designations identifying different types of portions of the reticle. An additional computer-implemented method includes determining a property of a manufacturing process used to process a wafer based on defects that alter a characteristic of a device formed on the wafer. Further computer-implemented methods include altering or simulating one or more characteristics of a design of an integrated circuit based on data generated by inspection of a wafer.

39 Claims, 9 Drawing Sheets

(51) Int. Cl.
*G01N 21/95* (2006.01)
*G01N 21/956* (2006.01)
*G03F 7/20* (2006.01)

(56) References Cited

U.S. PATENT DOCUMENTS

| | | | |
|---|---|---|---|
| 6,076,465 | A | 6/2000 | Vacca et al. |
| 6,381,358 | B1 | 4/2002 | Vacca et al. |
| 6,388,253 | B1* | 5/2002 | Su ................................ 250/310 |
| 6,513,151 | B1 | 1/2003 | Erhardt et al. |
| 6,529,621 | B1 | 3/2003 | Glasser et al. |
| 6,557,162 | B1* | 4/2003 | Pierrat ............................. 716/55 |
| 6,566,885 | B1 | 5/2003 | Pinto et al. |
| 6,714,885 | B1 | 3/2004 | Lee |
| 6,868,175 | B1* | 3/2005 | Yamamoto et al. ........... 382/145 |
| 6,968,527 | B2* | 11/2005 | Pierrat .............................. 430/5 |
| 7,135,344 | B2 | 11/2006 | Nehmadi et al. |
| 7,221,891 | B2* | 5/2007 | Matsumoto et al. .......... 399/262 |
| 7,297,453 | B2* | 11/2007 | Watson et al. ................. 430/30 |
| 2002/0057831 | A1 | 5/2002 | Hiroi et al. |
| 2002/0121915 | A1* | 9/2002 | Alonso Montull et al. ... 324/765 |
| 2002/0126888 | A1 | 9/2002 | Vacca et al. |
| 2003/0022401 | A1 | 1/2003 | Hamamatsu et al. |
| 2003/0025904 | A1* | 2/2003 | Sakai et al. ................. 356/237.2 |
| 2003/0058444 | A1* | 3/2003 | Nara et al. .................... 356/394 |
| 2003/0154461 | A1* | 8/2003 | Pierrat ............................. 716/21 |
| 2003/0212469 | A1* | 11/2003 | Wang et al. ................... 700/121 |
| 2003/0217343 | A1 | 11/2003 | Rajsuman et al. |
| 2004/0008880 | A1 | 1/2004 | Horie et al. |
| 2004/0015806 | A1 | 1/2004 | Frank et al. |
| 2004/0038454 | A1* | 2/2004 | Coldren et al. ............... 438/122 |
| 2004/0078724 | A1 | 4/2004 | Keller et al. |
| 2004/0254752 | A1 | 12/2004 | Wisniewski et al. |
| 2005/0010890 | A1 | 1/2005 | Nehmadi |
| 2005/0168731 | A1* | 8/2005 | Shibuya et al. ............. 356/237.4 |
| 2007/0023658 | A1* | 2/2007 | Nozoe et al. .................. 250/310 |
| 2009/0007030 | A1 | 1/2009 | Nehmadi et al. |

FOREIGN PATENT DOCUMENTS

| | | |
|---|---|---|
| JP | Hei 9-148386 | 6/1997 |
| JP | 9-211840 | 8/1997 |
| JP | 10-293393 | 11/1998 |
| JP | 2000-147748 | 5/2000 |
| JP | 2001-033941 | 2/2001 |
| JP | 2002-148027 | 5/2002 |
| JP | 2002-323749 | 11/2002 |
| JP | 2002-328462 | 11/2002 |
| JP | 2003-23056 | 1/2003 |
| WO | 99/59200 | 11/1999 |
| WO | 00/36525 | 6/2000 |
| WO | 01/40145 | 6/2001 |
| WO | 02/075973 | 9/2002 |
| WO | WO2004/040626 | 5/2004 |

OTHER PUBLICATIONS

International Search Report, PCT/US2004/021459, mailed Jun. 9, 2005.
Cai et al., "Enhanced Dispositioning of Reticle Defects Using the Virtual Stepper with Automated Defect Severity Scoring," Proceedings of SPIE, vol. 4409, 2001, pp. 467-478.
Cai et al., "Automated Defect Severity Analysis for Binary and PSM Mask Defects," Proceedings of SPIE, vol. 4889, 2002, pp. 253-262.
European Search Report, EP 04777530, mailed Jul. 27, 2006.
Genut, "Chemically Assisted Laser Removal of Photoresist and Particles from Semiconductor Wafers," Fine Particle Society, Apr. 1988, 10 pages.
U.S. Provisional Patent Application for CAD Information in DMS and Other Applications, filed Jul. 11, 2003 under U.S. Appl. No. 60/486,565.
Declaration of Youval Nehmadi, executed on May 31, 2006, filed in U.S. Appl. No. 10/780,377, filed Feb. 17, 2004.
Notice of the Reasons for Refusal for Japanese Patent Application No. 2010-287241 mailed Apr. 2, 2013.
Notice of the Reasons for Refusal for Japanese Patent Application No. 2010-287241 mailed Nov. 26, 2013.
Notice of the Reasons for Refusal for Japanese Patent Application No. 2013-161037 mailed May 27, 2014.
Office Action for Chinese Patent Application No. 200480025041.0 mailed Apr. 28, 2014 (no translation available).
Notification of Ex Officio Provisional Refusal for Korean Application No. 10-2006-7000200 mailed Feb. 17, 2011.
Official Action for Japanese Patent Application No. 2006-518815 mailed Jun. 29, 2010.

* cited by examiner

Frame AND Data = M1 Layer

Frame NOT M1 Layer = Dummy

Frame AND Dummy = DCA1

DCA1 NOT M2 Layer = DCA2

METHODS AND SYSTEMS FOR INSPECTION OF WAFERS AND RETICLES USING DESIGNER INTENT DATA

PRIORITY CLAIM

This application claims priority to U.S. Provisional Application No. 60/485,338 entitled "Methods and Systems for Inspection of Wafers and Reticles Using Designer Intent Data," filed Jul. 3, 2003, which is incorporated by reference as if fully set forth herein.

BACKGROUND OF THE INVENTION

1. Field of the Invention

The present invention generally relates to methods and systems for inspection of wafers and reticles using designer intent data. Certain embodiments relate to systems and methods for detecting defects on a wafer based on data representative of a reticle or data produced by inspection of a reticle.

2. Description of the Related Art

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

During each semiconductor fabrication process, defects such as particulate contamination and pattern defects may be introduced into semiconductor devices. Such defects may be found either randomly on a specimen surface or may be repeated within each device formed on a specimen. For example, random defects may be caused by events such as an unexpected increase in particulate contamination in a manufacturing environment and an unexpected increase in contamination in process chemicals that may be used in fabrication of a semiconductor device. Defects may also be formed in a systematic fashion over time and due to individual process marginalities and interactions of multiple processes. Defects caused by individual process marginalities or by interactions between multiple processes may result in defects such as a film thickness variation or a lateral dimension variation due to dose variation. Such defects may, in turn, result in a defect in a semiconductor device formed on the specimen such as bridging between two conductive structures thereby forming a short between the structures. Defects repeated within each semiconductor device formed on an entire specimen may, for example, be systematically caused by contamination or defects found on a reticle, or a mask. Contamination or defects on a reticle may be transferred along with a device pattern to a resist during a lithography process.

As the dimensions of advanced semiconductor devices continue to shrink, the presence of defects in the semiconductor devices limits the successful fabrication, or yield, of a semiconductor device. For example, a reticle defect reproduced in a resist patterned during lithography may cause an open circuit or a short circuit in a semiconductor device formed in subsequent processing. Because fabrication of a semiconductor device includes many complex process steps, the adverse effects of defects on total yield may increase exponentially if an error that is caused by a defect is propagated throughout an entire manufacturing process or operation over time.

SUMMARY OF THE INVENTION

An embodiment of the invention relates to a computer-implemented method that includes identifying nuisance defects on a wafer based on inspection data produced by inspection of a reticle. The reticle is used to form a pattern on the wafer prior to inspection of the wafer. The nuisance defects may be formed on the wafer as a result of defects on the reticle that were determined to be permissible reticle defects. In one embodiment, the nuisance defects may be formed on the wafer as a result of defects on the reticle that were determined to be permissible reticle defects based on designer intent data. In further embodiments, if the nuisance defects are formed on the wafer as a result of defects on the reticle that were determined to be permissible reticle defects, the method may include analyzing the nuisance defects to determine if the permissible reticle defects were correctly classified. In some embodiments, if the permissible reticle defects were not correctly classified, the method may include determining if the reticle should be analyzed, reworked, or disposed. In another embodiment, the method may include determining if the nuisance defects will affect yield of semiconductor devices, which will be formed on the wafer.

In some embodiments, the method may include separating the nuisance defects from actual defects on the wafer. Such embodiments may also include processing data representative of the actual defects, but not the nuisance defects. In additional embodiments, the method may include generating a two-dimensional map of the wafer. The nuisance defects may be distinguished from other defects in the map by one or more different designations.

In another embodiment, the method may include transmitting the inspection data from an inspection system used to perform the inspection of the reticle to a processor configured to perform the method. In a different embodiment, the method may include transmitting the inspection data from a fab database to a processor configured to perform the computer-implemented method. In one such embodiment, transmitting the inspection data may include sending coordinates of defects detected on the reticle and images of the defects. In an additional embodiment, if the inspection data includes coordinates of a location of a defect on the reticle, the method may include translating the coordinates of the location of the defect to coordinates of locations of one or more of the nuisance defects on the wafer. The method may include any other steps of any of the methods described herein.

An additional embodiment relates to a computer-implemented method that includes identifying locations on a wafer in which nuisance defects will be formed based on inspection data produced by inspection of a reticle. In one embodiment, the method may also include selecting one or more parameters for wafer inspection such that the locations of the nuisance defects are not inspected. In a different embodiment, the method may include selecting one or more parameters for wafer defect review such that the nuisance defects are not reviewed. In another embodiment, the method may include selecting one or more parameters for wafer defect analysis such that the nuisance defects are not analyzed.

Another embodiment relates to a computer-implemented method that includes identifying critical portions of a wafer based on the criticality associated with different areas of the wafer. The method also includes selecting parameters for inspection of the wafer such that only the critical portions of the wafer are inspected. In some embodiments, the parameters may be selected such that nuisance defects on the wafer are not classified as actual defects. In one embodiment, the parameters may be selected such that critical portions of the wafer having different criticalities are inspected with different parameters. According to another embodiment, the method may include setting one or more parameters for classification of defects on the wafer based on the criticality of the critical portions.

In another embodiment, the method may include assigning a designation to a defect on the wafer based on the criticality of the critical portion in which the defect is located. In a different embodiment, the method may include determining processing of a defect on the wafer based on the criticality of the critical portion in which the defect is located. In some embodiments, the method may include classifying defects on the wafer as critical defects or non-critical defects and analyzing a process performed on the wafer based on the critical defects and the non-critical defects. In another embodiment, the method may include classifying defects on the wafer as critical defects or non-critical defects and processing the critical defects separately from the non-critical defects.

According to an additional embodiment, the method may include discarding inspection data representing defects in one of the critical portions if the defects have a lateral dimension smaller than a predetermined threshold and if other features in the one portion have a lateral dimension greater than the predetermined threshold. In a different embodiment, the method may include discarding inspection data representing defects in one of the critical portions if an element of a circuit in the one portion has a predetermined amount of redundancy and if the defects in the one portion do not exceed a predetermined density threshold.

In some embodiments, the method may include translating coordinates of a location of a defect detected on a reticle to coordinates of locations of one or more defects on the wafer. Such an embodiment may also include analyzing the printability of the defect detected on the reticle. In another such embodiment, the method may include removing inspection data at the coordinates on the wafer from the wafer inspection data.

In one embodiment, the method may include generating one or more two-dimensional maps illustrating the critical portions of the wafer. The inspection may be performed on one level of the wafer. In one embodiment, the method may include identifying the criticality of a defect on the wafer based on the criticality of the critical portion in which the defect is located and data representative of at least one layer of the wafer above or below the one level. In another embodiment, the method may include generating a three-dimensional representation of the defect, the one level, and at least the one layer of the wafer above or below the one level.

A further embodiment relates to a computer-implemented method that includes determining one or more parameters for wafer defect review based on the criticality associated with different areas of the wafer. In one embodiment, the method may include selecting the one or more parameters such that only defects located in critical portions of the wafer are reviewed. In one such embodiment, the one or more parameters may be different for one or more of the critical portions. In another embodiment, the method may include sending information about the criticality of the different areas of the wafer to a tool configured to perform the wafer defect review.

Another embodiment relates to a computer-implemented method that includes determining one or more parameters for wafer defect analysis based on the criticality associated with different areas on the wafer. The method may include selecting the one or more parameters such that only defects located in critical portions of the wafer are analyzed in some embodiments. In such an embodiment, the one or more parameters may be different for one or more of the critical portions. In other embodiments, the method may include sending information about the criticality of the different areas of the wafer to a tool configured to perform the wafer defect analysis.

An additional embodiment relates to a computer-implemented method that includes identifying bad die on a wafer. In an embodiment, identifying the bad die may include performing functional testing on the wafer after a manufacturing process used to process the wafer is completed. The bad die may contain one or more electrical elements having functionality outside of a predetermined range. The method also includes identifying a first portion of defects and a second portion of defects on the wafer based on data generated by inspection of the wafer in combination with information representative of a design of the one or more electrical elements. In one embodiment, the data generated by inspection of the wafer may include data generated by multiple inspections of the wafer, which may be performed at different times during the manufacturing process. The first portion of the defects may alter a characteristic of a device formed by the one or more electrical elements such that the characteristic is outside of the predetermined limits. In addition, the method may include determining a property of the manufacturing process based on the first portion of the defects. In one embodiment, the property may be a kill ratio of the first portion of the defects. In a different embodiment, the property may be a yield of the manufacturing process. In some embodiments, the method may include altering one or more parameters of the manufacturing process based on the property. The method may further include any other steps of any of the methods described herein.

A further embodiment relates to a computer-implemented method that includes altering a design of an integrated circuit (IC) based on data generated by inspection of a wafer during a manufacturing process. The data generated by inspection of the wafer includes information about defects detected on the wafer, and a substantial portion of the defects includes critical defects that can alter one or more characteristics of the IC. For example, the method may include distinguishing between the critical defects and other non-critical defects detected during the inspection based on the design. The non-critical defects are defects that will not substantially alter the one or more characteristics of the IC.

In one embodiment, altering the design may be performed using a feedback control technique. In another embodiment, altering the design may include altering the design of the IC to reduce a number of the critical defects that are formed during the manufacturing process. In an additional embodiment, the method may include identifying individual processes of the manufacturing process that result in at least some of the critical defects being formed on the wafer. In one such embodiment, the method may also include determining if the design of the IC contributes to the formation of the critical defects. Such embodiments may also include altering the design of the IC to reduce the number of the critical defects that are formed during the individual processes. In another embodiment, the method may include determining a yield of the manufacturing process based on the critical defects. Such an embodiment may also include altering the design of the IC to increase the yield of the manufacturing process. Yet another embodiment may include altering the manufacturing process based on the data. The method may further include any other steps of any of the methods described herein.

An additional embodiment relates to a storage medium. The storage medium includes data representative of an IC design. The storage medium also includes data representative of an IC manufacturing process. In addition, the storage medium includes defect data representative of defects detected on a wafer during the IC manufacturing process. The defect data may be filtered such that a substantial portion of the defects includes critical defects that can alter one or more characteristics of the IC. The storage medium can be used to alter the IC design based on the data representative of the IC design, the data representative of the IC manufacturing process, and the defect data. In one embodiment, the storage medium may also include data representative of relationships between the critical defects and the IC design. The storage medium may be further configured as described herein.

Another embodiment relates to a computer-implemented method that includes simulating one or more characteristics of an IC based on data generated by inspection of a wafer during a manufacturing process. In one embodiment, the one or more characteristics include, but are not limited to, voltage drops, timing slowdowns, partial device failure, and total device failure. The data may include information about defects detected on the wafer. In an embodiment, the information about the defects may include coordinates of defect locations and three-dimensional defect profiles. A substantial portion of the defects include critical defects that can alter the one or more characteristics of the IC. In one embodiment, the method may also include distinguishing between the critical defects and other non-critical defects detected during the inspection based on the design. The non-critical defects will not substantially alter the one or more characteristics of the IC. The method may further include any other steps of any of the methods described herein.

An additional embodiment relates to a computer-implemented method that includes determining placement of a pattern on a specimen based on data generated by inspection of the specimen. In some embodiments, determining the placement of the pattern may include laterally translating the pattern, rotating the pattern, scaling the pattern, or any combination thereof. In an embodiment, the specimen may be a blank reticle substrate. In a different embodiment, the specimen may be a wafer. In some embodiments, determining the placement of the pattern may include selecting the placement of the pattern such that a substantial portion of defects on the specimen does not overlap with the pattern. In another embodiment, the method may include identifying critical portions of the pattern based on design information. In such an embodiment, determining placement of the pattern may include determining the placement of the critical portions of the pattern with respect to locations of defects on the specimen. In yet another embodiment, determining placement of the pattern may include selecting the placement of the pattern such that a substantial portion of defects on the specimen does not overlap with critical portions of the pattern. In a different embodiment, determining placement of the pattern may include selecting the placement of the pattern such that an amount of overlap between defects on the specimen and critical portions of the pattern is below a predetermined threshold.

In another embodiment, if the specimen is a reticle, the method may include determining an amount of overlap between defects on the reticle and critical portions of the pattern. Such an embodiment may also include estimating the number of critical defects that would be produced on a wafer that is exposed with the reticle. In a further embodiment, if the specimen is a reticle, the method may include determining alignment of the reticle with an exposure tool or a wafer based on the placement of the pattern with respect to a coordinate system. The method may further include any other steps of any of the methods described herein.

Another embodiment relates to a computer-implemented method that includes determining a design significance of a defect detected on a reticle. The design significance may be a measure of how the defect impacts a design of the reticle. The method may also include determining a lithographic significance of the defect. The lithographic significance may be a measure of how the defect impacts a wafer patterned by a lithography process that uses the reticle. In addition, the method may include determining an overall significance of the defect based on the design significance and the lithographic significance. The overall significance may be selected from the group consisting of lithographically and design significant, lithographically significant only, design significant only, and not significant.

In an embodiment, the method may include determining a design significance of different regions on the reticle. In such an embodiment, determining the design significance of the defect may be based on the design significance of the region on the reticle in which the defect is located. In another embodiment, determining the design significance may include comparing data representative of the defect to a threshold and determining that the defect has design significance if the data is greater than the threshold. In some embodiments, the threshold may vary depending on a location of the defect on the reticle.

In one embodiment, the method may include determining a lithographic significance of different regions on the reticle. In one such embodiment, determining the lithographic significance of the defect may be based on the lithographic significance of the region on the reticle in which the defect is located. In an additional embodiment, determining the lithographic significance of a defect may include comparing data representative of the defect to a threshold and determining that the defect has lithographic significance if the data is greater than the threshold. In some embodiments, the threshold may vary depending on a location of the defect on the reticle.

In another embodiment, the method may include determining an overall significance of different regions on the reticle. In one such embodiment, the method may include determining one or more parameters of a process used to fabricate the different regions of the reticle based on the overall significance of the different regions. In a different such embodiment, the method may include altering one or more parameters of a process used to inspect the different regions of the reticle based on the overall significance of the different regions. In yet another such embodiment, the method may include altering one or more parameters of a process used to repair the reticle based on the overall significance of the different regions. In this manner, a process used to fabricate, inspect, or repair a reticle may have one or more parameters in one of the different regions that are different than the one or more parameters of the process in another of the different regions.

In some embodiments, the method may include determining one or more parameters of a process that is used to repair the defect based on the overall significance of the defect. The one or more parameters used to repair different defects on the reticle may be different. In another embodiment, the method may include determining processing of the reticle based on the overall significance of the defect. The processing may include rejecting the reticle, repairing the reticle, or cleaning the reticle.

In an additional embodiment, the method may include generating a visual representation of the defect. The visual representation may include one or more designations assigned to the defect indicating the overall significance of the defect. In a different embodiment, the method may include generating a visual representation of individual regions on the reticle. Such a visual representation may include designations assigned to the individual regions indicating the overall significance of the individual regions. The method may further include any other steps of any of the methods described herein.

Further embodiments relate to a carrier medium that includes program instructions executable on a computer system to perform any of the computer-implemented methods described herein. Additional embodiments relate to a system configured to perform any of the computer-implemented methods described herein. For example, the system may include a processor configured to execute program instructions for performing one or more of the computer-implemented methods described herein. In one embodiment, the system may be a stand-alone system. In another embodiment, the system may be a part of or coupled to an inspection system. In a different embodiment, the system may be a part of or coupled to a defect review system. In yet another embodiment, the system may be coupled to a fab database. For example, the system may be coupled to an inspection system, a review system, or a fab database by a transmission medium such as a wire, a cable, a wireless transmission path, and/or a network. The transmission medium may include "wired" and "wireless" portions.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
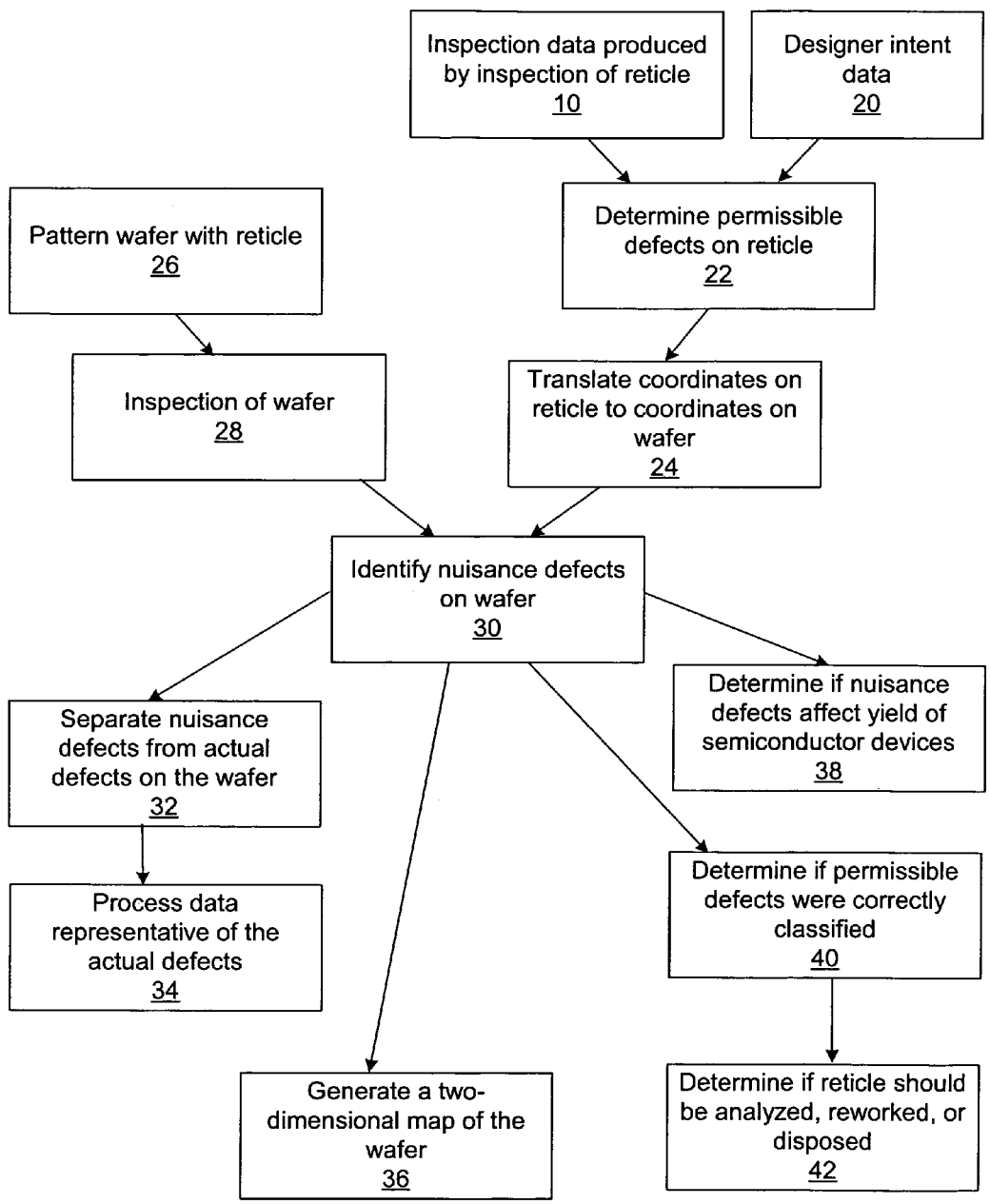
FIG. 1 is a flow chart illustrating an embodiment of a computer-implemented method that includes identifying nuisance defects on a wafer based on reticle inspection data.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include only the substrate such as a virgin wafer. Alternatively, a wafer may include one or more layers that may be formed upon a substrate. For example, such layers may include, but are not limited to, a resist, a dielectric material, and a conductive material. A resist may include a resist that may be patterned by an optical lithography technique, an e-beam lithography technique, or an X-ray lithography technique. Examples of a dielectric material may include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials such as "xerogels," and "high-k" dielectric materials such as tantalum pentoxide. In addition, examples of a conductive material may include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed.

A "reticle" or a "mask" is generally defined as a substantially transparent substrate having substantially opaque regions and/or partially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source.

As used herein, the term "designer intent data" is used interchangeably with the term "design information." In addition, although some embodiments are described herein with respect to an integrated circuit, it is to be understood that these embodiments may be similarly applied to other semiconductor devices such as microelectromechanical (MEMS) devices and the like. In addition, the term "integrated circuit" is used interchangeably herein with the term "semiconductor device."

Turning now to the drawings, it is noted that the steps shown in each of the figures are not essential to practice of the respective methods. One or more steps may be omitted from or added to any of the methods illustrated in each of the figures, and the methods can still be practiced within the scope of these embodiments. FIG. 1 is a flow chart illustrating a computer-implemented method that includes identifying nuisance defects on a wafer based on inspection data produced by inspection of a reticle. The method illustrated in FIG. 1 provides an improved method of wafer inspection, wafer defect classification, wafer defect review, and wafer defect analysis by utilizing designer intent data.

As shown in FIG. 1, the method may include obtaining inspection data produced by inspection of a reticle, as shown in step 10. Obtaining the inspection data may include inspecting the reticle. In some embodiments, obtaining the inspection data may include receiving the inspection data from an inspection system used to inspect the reticle. In other embodiments, obtaining the inspection data may include receiving the inspection data from a fab database. A fab database may include information related to any of the processes performed in a fab such as tool history, wafer history, and reticle history. A fab database may also include any set of data suitable for use in an overall fab management system. An example of such a system is illustrated in PCT Publication No. WO 99/59200 to Lamey et al., which is incorporated by reference as if fully set forth herein. The data may be processed by a processor coupled to the inspection system prior to being sent to a processor configured to perform the method or to the fab database. In addition, or alternatively, the data may be processed after being received by the processor configured to perform the method.

Figure 2:
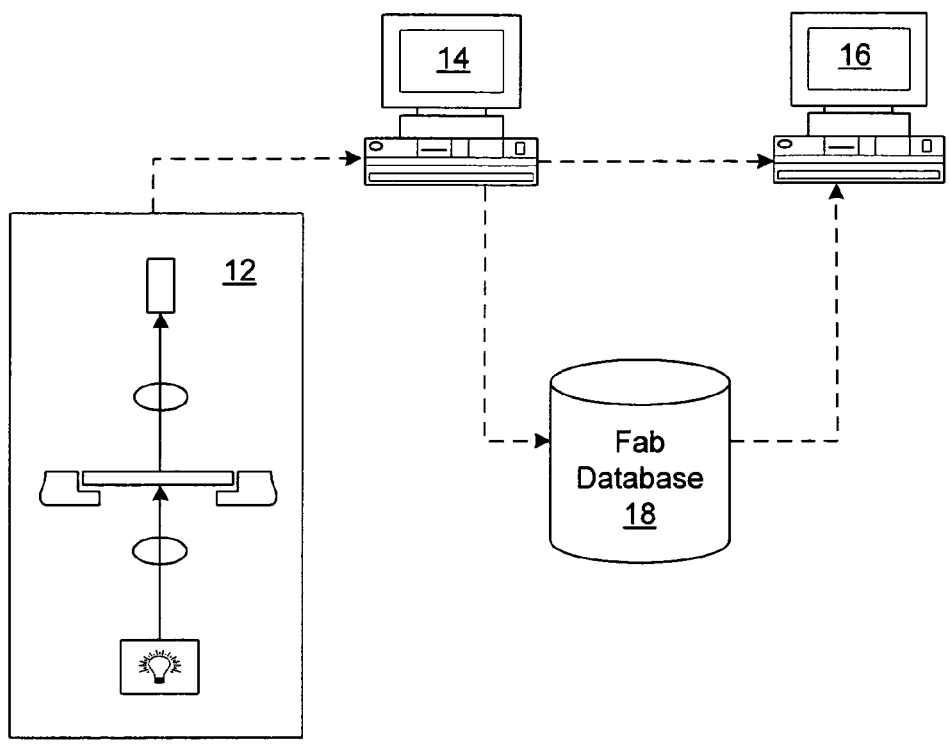
FIG. 2 is a schematic diagram illustrating an inspection system coupled to a processor, which is coupled to a fab database and/or a processor configured to perform a computer-implemented method described herein.

As shown in the schematic diagram of FIG. 2, for example, inspection system 12 may be used to inspect a reticle. In this manner, the inspection system will generate inspection data during inspection of a reticle. The individual components of inspection system 12 shown in FIG. 2 are known in the art and thus will not be described further herein. Although one configuration of a reticle inspection system is shown in FIG. 2, the inspection system may include any reticle inspection system known in the art. Examples of appropriate inspection systems include the SL3UV system and the TeraStar system available from KLA-Tencor, San Jose, Calif. In addition, the inspection system may be an aerial imaging based reticle inspection system. The inspection data may be received by processor 14, which is coupled to the inspection system. In some embodiments, processor 14 may be incorporated into the inspection system. The data may then be transmitted from processor 14 to processor 16, which is configured to perform the method. In some embodiments, processor 16 may be an image computer. In addition, processor 16 may include any suitable processor known in the art. In a different embodiment, the inspection data may be transmitted from processor 14 to fab database 18. The data may then be transmitted from the fab database to processor 16. In any of the above embodiments, the data may be transmitted as files having a common data structure (such as KLARFF, which is commercially available from KLA-Tencor) that may be used or interpreted by both of the processors.

Inspection system 12, processors 14 and 16, and fab database 18 may be coupled, as shown in FIG. 2, by transmission media such as wires, cables, wireless transmission paths, and/or a network. The transmission media may include "wired" and "wireless" portions. In some embodiments, processor 16 may be incorporated into a wafer inspection system (not shown). In other embodiments, processor 16 may be a stand-alone processor. In either embodiment, processor 16 may be coupled to a wafer inspection system such that the processor may receive data generated by inspection of wafers. In other embodiments, processor 16 may receive wafer inspection data from fab database 18. In some embodiments, the data which is transmitted to processor 16 may include coordinates of defects detected on the reticle and images of the defects.

Traditionally, integrated circuit (IC) design and IC manufacturing have been markedly separate activities with minimal overlap. However, today's state of the art manufacturing technology requires substantial interaction between these two activities. The place where most of this collaboration takes place is at the TCAD layout phase, where the schematics from IC designers are physically placed and routed. This collaboration, which is commonly referred to as "Design for Manufacturability" (DFM), has raised numerous problems for wafer inspection. The methods described herein, however, address many of these problems.

For example, as shown in FIG. 1, inspection data 10 produced by inspection of a reticle may be used in combination with designer intent data 20 to determine permissible defects on the reticle, as shown in step 22. The designer intent data may include designations identifying different types of regions of the reticle, different types of features on the reticle, and/or different portions of features on the reticle. The different types of regions, features, or portions of features may include, for example, critical and non-critical regions, features, or portions of features as described in more detail herein. The designations may vary depending upon a circuit pattern database generated from an IC design. The IC design may be developed using any method or system known in the art such as electronic design automation (EDA), computer aided design (CAD), and other IC design software. Such methods and systems may be used to generate the circuit pattern database from the IC design. The circuit pattern database includes data representing a plurality of layouts for various layers of the IC. Therefore, data in the circuit pattern database may be used to determine layouts for a plurality of reticles. A layout of a reticle generally includes a plurality of polygons that define features in a pattern on the reticle. Each reticle is used to fabricate one of the various layers of the IC. The layers of the IC may include, for example, a junction pattern in a semiconductor substrate, a gate dielectric pattern, a gate electrode pattern, a contact pattern in an interlevel dielectric, and an interconnect pattern on a metallization layer.

A circuit pattern database may include designations as described above. The designations may include, for example, flags or tags associated with different types of regions, features, or portions of features on the reticle. The designations, however, may include any indicia suitable to distinguish one type of region, feature, or portion of a feature from another type. Each region, feature, or portion of a feature, or only some of the regions, features, or portions of features, on the reticle may be associated with a designation. Data in the circuit pattern database representing a layout of a reticle may be separate from data in the circuit pattern database representing the designations. In addition, different types of designations may be separated in the circuit pattern database. For example, the circuit pattern database may include a first set of data that includes designations for critical regions, features, or portions of features on the reticle and a second set of data that includes designations for non-critical regions, features, or portions of features on the reticle. Alternatively, different designations may be combined into a single set of data. Data representing a layout of a reticle and designations may have any form readable by a processor coupled to an inspection system or another processor. For example, the data may include files or other readable data including one or more features and spatial positions within the reticle associated with the features. Each feature may also include one or more polygons or other shapes as described herein, and a spatial position within the reticle may also be associated with each of the polygons or shapes. Therefore, the data can be used to fabricate a reticle.

Additional examples of designer intent data and methods of use for reticle inspection are illustrated in U.S. Pat. No. 6,529,621 to Glasser et al. and PCT Application No. WO 00/36525 by Glasser et al., which are incorporated by reference as if fully set forth herein. A system or method as described herein may also include any of the elements or steps illustrated by Glasser et al. The designer intent data may be provided directly to a processor of a wafer inspection system, a defect review tool, and/or a defect analysis station. In one example, the designer intent data may be sent directly to the processor of the wafer inspector, the defect review tool, and/or the defect analysis station via a transmission medium such as that described above. One example of an analysis station is the Klarity defects product, which is commercially available from KLA-Tencor. The Klarity defects product provides offline analysis of data that is taken from a wafer inspector.

Some reticles include phase shift or optical proximity correction (OPC) features. In one embodiment, the method may include simulating the printability of such a reticle on a wafer. The simulation may be performed using a simulation program such as PROLITH, which is available from KLA-Tencor, or any other suitable simulation program known in the art. The simulation may be based on data representative of the reticle and/or data generated by inspection of the reticle. In addition, the method may include distinguishing between critical defects and non-critical defects on the reticle based on the simulation results and designer intent data. In another embodiment, the method may include removing the phase shift or OPC features from the data representative of the reticle. The phase shift or OPC features may be removed using a simulation program such as PROLITH. Designer intent data may then be used to identify non-critical defects on the reticle and to optionally filter out non-critical defects on the reticle. Removing phase shift or OPC features from the reticle data may simplify distinguishing between critical defects and non-critical defects on the reticle.

Permissible defects may be identified as defects on the reticle that are located in non-critical portions of the reticle. In some instances, permissible defects may be identified as defects that are located proximate a non-critical feature on the reticle such as a test structure. In addition, permissible reticle defects may be identified as defects that have lateral dimensions that are smaller than a predetermined range of lateral dimensions or a predetermined threshold for the lateral dimensions. Alternatively, permissible reticle defects may be identified as reticle defects that do not alter a characteristic of the reticle such as phase and transmission such that the characteristic is outside of a predetermined range for the characteristic. In other instances, permissible reticle defects may be identified as defects that will not print on a wafer exposed with the reticle. Alternatively, permissible reticle defects may be identified as defects on the reticle that will not alter a pattern that is printed on a wafer exposed with the reticle such that the pattern will not have one or more characteristics that are outside of a predetermined range for the characteristics. For example, a permissible defect may be a reticle defect that may alter a lateral dimension of a feature printed on a wafer, but does not alter the lateral dimension such that it is outside of an acceptable range of lateral dimensions.

In general, permissible reticle defects may be any defect found on a reticle that will not alter a characteristic of a reticle, a critical portion of a reticle, a pattern on a wafer, or a critical portion of a wafer such that the characteristic is outside of a predetermined range for the characteristic. In this manner, permissible defects on a reticle may not be repaired prior to releasing the reticle for fabrication. Tolerating permissible reticle defects will result in such defects being repeatedly printed on wafers. Therefore, the permissible reticle defects may alter a pattern printed on a wafer with the reticle such that the printed pattern deviates from the "ideal" pattern. As such, changes in the pattern on the printed wafer caused by permissible reticle defects may be identified as defects on the wafer during inspection of the wafer. Wafer inspection systems will flag these defects (since they will generally show up as differences in array or random detection modes). At the same time, there may be other repeating defects on the wafer that will be interesting to users. Therefore, in a wafer inspection process, numerous repeating defects may be found, some of which may be "nuisance defects," and users will have to analyze these repeater defects in defect classification and review. In this manner, applying designer intent data to reticle inspection without also adapting wafer inspection processes to use designer intent principles will pose real problems for wafer inspection, defect classification and review. As a result, the wafer inspection results may be skewed by permissible wafer defects resulting from permissible reticle defects. In addition, the accuracy and throughput of defect classification and review may be significantly reduced. The method described herein, however, advantageously provides a method for determining which defects are "critical defects" and which defects are merely nuisance defects. In this manner, the method described herein prevents wafer inspection systems or processors from being flooded with numerous false defects caused by permissible reticle defects. Therefore, the method described herein provides wafer inspection results that may be more clearly analyzed and utilized.

As used herein, the term "nuisance defects" generally refers to defects on a wafer that do not alter a pattern formed on the wafer such that electrical elements formed from the pattern will have one or more characteristics within a predetermined range for the characteristics. In contrast, as used herein, the term "critical defects" generally refers to defects on a wafer that alter a pattern formed on the wafer such that electrical elements formed from the pattern will have one or more characteristics outside of a predetermined range for the characteristics. In some embodiments, critical defects may be distinguished from nuisance defects or other "non-critical defects" by comparing the defects or features on the patterned wafer that are affected by the defects to design limits for the patterned wafer. Critical defects may be classified as those defects that alter the patterned wafer such that it has one or more characteristics outside of the design limits.

The method may also include patterning a wafer using the reticle, as shown in step 26. Patterning a wafer generally includes forming a layer of a resist on the wafer. The wafer and the layer of resist formed thereon may be placed in an exposure tool. The exposure tool generally exposes the layer of resist by directing light through the reticle and onto the resist. The exposure tool may be a scanning projection system or a step-and-repeat system, also called a "stepper." The exposure tool may include any exposure tool known in the art such as tools commercially available from Nikon, ASM Lithography, Canon, or Integrated Solutions, Inc. After the resist has been exposed, the wafer may be developed such that a portion of the resist is removed. The remaining portions of the resist form a pattern on the wafer.

The method further includes inspecting the wafer, as shown in step 28. The wafer may be inspected using any method known in the art. For example, the wafer may be inspected by illuminating the wafer at an oblique angle of incidence and detecting light scattered from the wafer. Alternatively, or in addition, the wafer may be inspected by detecting light specularly reflected from the wafer. In addition, the wafer may be inspected using optical techniques or non-optical techniques such as an e-beam inspection technique. The wafer may also be inspected using any inspection system known in the art. Examples of suitable inspection systems include the 2351 system, the AIT XP system, the AIT TFH system, the eS25 system, the Surfscan SP1$^{DLS}$ system, the Viper 2401 system, and the Viper 2430 system, which are all available from KLA-Tencor. In some embodiments, the method may not include inspecting the wafer. In such embodiments, the method may include obtaining wafer inspection data from a wafer inspection system or a fab database. The wafer inspection data may be obtained from a wafer inspection system or a fab database as described and shown in FIG. 2.

In addition, the method includes identifying nuisance defects on the wafer, as shown in step 30. The nuisance defects may be identified based on inspection data produced by inspection of a reticle that was used to form a pattern on the wafer prior to inspection of the wafer. For example, nuisance defects may be formed on the wafer as a result of defects on the reticle that were determined to be permissible reticle defects. In this manner, the method may include identifying reticle defects that were determined to be permissible and locating corresponding wafer defects that result from these permissible reticle defects. Since it is known that these defects are permissible and will not reduce yield of semiconductor devices, the processor configured to perform the method may be provided with data relating to permissible reticle defects such as defect location and other defect characteristics (i.e., size, aspect ratio, etc.), which may be generated during the reticle inspection process. For example, a processor configured to perform the method may receive reticle inspection data for the reticle that was used to pattern the wafer as described above. The processor may identify wafer defects corresponding to the permissible reticle defects and may not flag these defects as "actual defects." The term "actual defects" is used herein to refer to defects on a wafer that are not a result of permissible reticle defects.

In addition, as shown in FIG. 1, the method may include translating coordinates of a location of a defect on a reticle to coordinates of one or more locations on a wafer, as shown in step 24. In some embodiments, the coordinates of a location of a permissible reticle defect may be translated to coordinates of one or more locations on a wafer. In this manner, if a defect is detected at these one or more locations on the wafer, the defect may be identified as a permissible wafer defect, or a "nuisance defect." In other embodiments, if the effect of a reticle defect on a patterned wafer is unknown, the coordinates of the reticle defect may be translated to coordinates of one or more locations on a wafer. The wafer may be exposed with the reticle, and the one or more locations on the wafer may be inspected or otherwise analyzed to determine the printability of the reticle defect or the effect that the reticle defect has on the printed pattern.

In other embodiments, the method may include identifying locations on a wafer in which nuisance defects will be formed based on inspection data produced by inspection of a reticle. Such a method may also include selecting one or more parameters for wafer inspection such that the locations in which the nuisance defects will be formed are not inspected. In a similar manner, the method may include selecting one or more parameters for wafer defect review such that the nuisance defects are not reviewed. In yet another embodiment, the method may include selecting one or more parameters for wafer defect analysis such that the nuisance defects are not analyzed.

In one embodiment, defect coordinates between a point on a reticle and a corresponding point on a wafer may be translated automatically. In contrast, currently, translation of coordinates between a reticle and a corresponding wafer is usually performed in a non-automatic manner. For example, non-automatic translation of coordinates may be performed manually using a spreadsheet. Automatic translation of coordinates, however, may be particularly advantageous in connection with analysis of defects based on design information. One embodiment of coordinate translation may be implemented using X-LINK, which is commercially available from KLA-Tencor, and automating the X-LINK capability for creating translated coordinates from reticle coordinates and wafer coordinates. In such an embodiment, reticle defect images may also be sent to a processor configured to analyze the defects based on the design information. In some embodiments, translating the coordinates from a reticle to a wafer may also include automatically verifying the accuracy of the translation.

In some embodiments, reticle defects may be determined to be permissible reticle defects based on designer intent data as described above. In another embodiment, the method may include using the designer intent data in combination with the data generated by inspection of the wafer to identify nuisance defects on the wafer. For example, the designer intent data may be used to indicate different types of regions, features, or portions of features on the reticle. Therefore, the designer intent data may be similarly applied to corresponding regions, features, or portions of features on a wafer printed with the reticle. In this manner, the defects may be identified as nuisance defects or critical defects based on the types of regions, features, or portions of features on the wafer in which the defects are located. As such, the designer intent data may be used to identify nuisance defects on the wafer which may or may not be formed on the wafer as a result of permissible reticle defects. For example, the designer intent data may be used to identify nuisance defects on the wafer that are a result of a defective resist layer.

In one such example, the method may include using designer intent data corresponding to "dummy structures" such as chemical-mechanical polishing (CMP) dummy pads to identify areas on a wafer that a user does not care about the defectivity of (i.e., "don't care areas" or DCA). As used herein, the term "dummy structures" is used to refer to patterned features that do not form an electrical element of a semiconductor device. As described above, wafer inspection faces two main challenges: detecting the defects of interest and filtering out the nuisance defects. When CMP dummy pads are added to the layout of a design, the second challenge increases in significance since the time spent on filtering nuisance defects detected on dummy pads may increase significantly. In addition, as the number of dummy pads increases, the number of nuisance defects that may be detected on the dummy pads will increase. Furthermore, as the number of copper-based interconnects included in an IC increases, the number of layers of the IC that include CMP dummy pads increases significantly.

Manually identifying DCA around regions of CMP dummy pads may be extremely time consuming. The method described herein, however, reduces the time required for filtering nuisance defects or manually generating DCA by using layout tools or a processor to generate the DCA around the dummy pads for inspection purposes. Additionally, the dummy pad areas may be filtered out for inspection purposes while maintaining the sensitivity of defect inspection on circuit areas of the overall pattern.

Figure 3A:
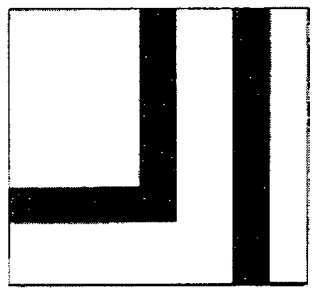
FIGS. 3a-3d are schematic diagrams illustrating one example of how individual layer data for an integrated circuit (IC) can be manipulated to identify "don't care areas" on a wafer.
Figure 3B:
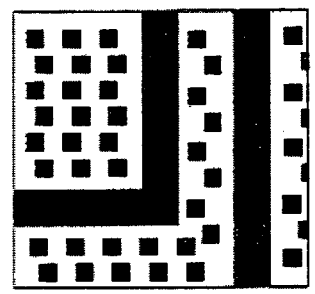

FIGS. 3a-3d illustrate one example of how individual layer data for an IC can be manipulated to identify DCA on a wafer. The individual layer data manipulated in this example is layer data for the first metal (M1) layer of the IC. However, it is to be understood that similar manipulation of individual layer data may be performed for any layer of an IC. Initially, the individual layer data may be selected from a GDSII file. By performing an AND operation between the individual layer data and the reference frame, the original mask data may be generated for the M1 layer, as shown in FIG. 3a. The dummy pads may then be generated in regions of the M1 layer where there is not a pattern by performing a NOT operation between the frame and the layer data, as shown in FIG. 3b. Therefore, a simple sequence of Boolean operations allows easy generation of dummy pads for the M1 layer.

Figure 3C:
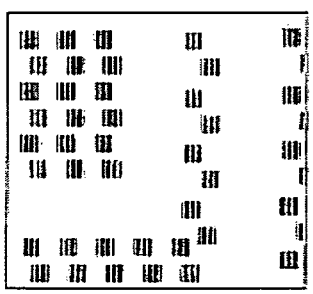
Figure 3D:
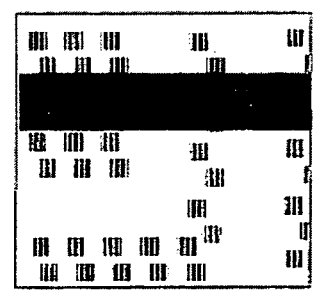

As shown in FIG. 3c, by performing an AND operation between the dummy data and the reference frame a first DCA (DCA1) may be identified. However, it may be advantageous to inspect some portions of DCA1 to check for defects that may adversely affect a layer above or below this layer. For example, most times a defect on a dummy pad by itself is insignificant from a circuit performance perspective. However, some of these defects may contribute to defects at another or the next layer, where they may cause disruption of a real circuit pattern. Manual generation of the DCA, however, is performed without any knowledge of the layers to be formed on top or below the layer for which the DCA is being determined. In contrast, by performing a NOT operation between the DCA1 data and data for a layer above or below this layer (i.e., in the case of the M1 layer, data for the M2, M3, and even M4 layers), the dummy area may be further filtered to determine the actual DCA data (i.e., DCA2). For example, as shown in FIG. 3d, the dummy areas that overlap with layer data of the M2 layer may be removed from DCA1 since defects on these overlapping dummy pads may adversely affect one or more characteristics of features on the M2 layer.

The method may also include altering the size of the DCA. For example, some of the DCA generated by the Boolean operations may have dimensions that are too small or too large to be effectively managed by an inspection system stage assembly and/or image computer. After generation of the DCA, the DCA may be sized down or up through the minimum dimension (i.e., x μm) that the inspection tool can handle (i.e., DCA3=DCA2−x or DCA3=DCA2+x). In addition, DCA that are relatively small may be eliminated from the DCA data for an entire layer. In this manner, certain DCA may be sized or eliminated from the DCA data for a layer while allowing identification of defects in the DCA that may cause defects on another layer of the IC.

The DCA data may be provided to a reticle inspection system, a wafer inspection system, a defect review system, and/or an analysis system. In another embodiment, designer intent data or information about the criticality associated with different areas of the wafer may be sent to a reticle inspection system, a wafer inspection system, a wafer defect review tool, and/or a wafer defect analysis tool. The reticle inspection system or the wafer inspection system may use the DCA data and/or the designer intent data to detect actual defects on a reticle or a wafer by filtering out nuisance defects detected in the DCA or by not performing inspection in the DCA at all. In this manner, the wafer inspector and/or reticle inspector may be configured to inspect only the areas of the wafer that matter or that matter the most.

In a similar manner, the defect review system may use the DCA data and/or the designer intent data to review only the areas of the wafer that matter (i.e., non-DCA areas) or that matter the most. In other words, one or more parameters for wafer defect review may be determined based on the criticality associated with different areas of the wafer. In one embodiment, the one or more parameters may be selected such that only defects located in critical portions of the wafer are reviewed. The parameters may also be different for different critical portions of the wafer. In addition, the defect review system may use the DCA data or designer intent data to distinguish between actual defects and nuisance defects. In another example, the defect analysis system may use the DCA data and/or the designer intent data to analyze only areas of the wafer that matter (i.e., non-DCA areas) or that matter the most. For example, one or more parameters for wafer defect analysis may be determined based on the criticality associated with different areas of the wafer. The one or more parameters may be selected such that only defects located in critical portions of the wafer are analyzed. The parameters may also be different for different critical portions of the wafer. Furthermore, the analysis station may use the DCA data or the designer intent data to distinguish between actual defects and nuisance defects.

In a different embodiment, data generated by a reticle or wafer inspection system may be transmitted to a processor configured to generate the DCA. The processor may use data generated by inspection in combination with the DCA data to identify actual defects on a reticle or wafer by filtering out defects detected in the DCA or by not performing defect detection on inspection data corresponding to the DCA.

The method may also include separating nuisance defects on the wafer from actual defects on the wafer, as shown in step 32. In one embodiment, the nuisance defects may be separated from the actual defects simply by not flagging or identifying the nuisance defects as defects at all. In this manner, data generated during wafer inspection will not include data representative of the nuisance defects. In other embodiments, nuisance and actual defects may be assigned different designations such that both types of defects are recorded and can be separated based on the different designations. In another embodiment, a nuisance defect file or list may be generated separately from an actual defect file or list. The nuisance defect file or list may or may not be accessible to the user. For example, in some instances, the user may be interested in only the actual defects and, therefore, will have no need for the nuisance defect file or list. In other instances, the user may access the list for further processing or analysis of the nuisance defects such as verification of the permissibility of the nuisance defects, determination of the effects of the nuisance defects on semiconductor device yield, or for display of the nuisance defects overlaid with other data. In other embodiments, the nuisance defect data may be used for tool-to-tool comparisons or calibrations. For example, the nuisance defect data may be used to calibrate or compare inspection systems of different make and model or inspection systems of the same make and model. If different makes and/or models of inspection systems are to be compared, the nuisance defects may be stored as files having a common data structure such as KLARFF.

As shown in step 34, the method may also include processing data representative of the actual defects, but not data representative of the nuisance defects. For example, the data representative of the nuisance defects may not be further processed, classified, reviewed, or analyzed since the defects were previously determined to be permissible. By eliminating processing of the nuisance defect data, processing the actual defect data will be simpler, possibly more accurate, and quicker. Processing data representative of the actual defects may include, but is not limited to, determining a lateral dimension of the actual defects, determining a material of the actual defects, classifying the actual defects, reviewing the actual defects, and analyzing a root cause of the actual defects.

In some embodiments, the method may include generating a two-dimensional map of the wafer, as shown in step 36. In one embodiment, the nuisance defects may be shown in the map along with other defects detected on the wafer. In such an embodiment, the nuisance defects may be distinguished from other defects in the map by one or more different designations. In other embodiments, the nuisance defects may not be shown in the map. The map may, therefore, illustrate only actual defects detected on the wafer. In this manner, the map may be more quickly analyzed by a user or by a processor since the nuisance defects have been eliminated. The two-dimensional map may illustrate the entire wafer (i.e., a wafer map) or only a portion of the wafer (i.e., one or more die maps). In one embodiment, the method may include generating more than one two-dimensional maps illustrating various portions of the wafer. In addition, the method may include generating one or more two-dimensional maps illustrating the critical portions of the wafer. The types of the various portions of the wafer may be illustrated in the maps using different colors, flags, or other indicia. In some embodiments, the two-dimensional map may be overlaid with other data such as PROLITH data, defects, and inspection areas.

In additional embodiments, the method may include determining if the nuisance defects affect the yield of semiconductor devices that are ultimately fabricated on the wafer, as shown in step 38. For example, the actual impact of the permissible reticle defects on yield may be analyzed from time to time. In one embodiment, the actual impact of the permissible reticle defects may be analyzed by electrical testing that is performed on electrical elements formed on the patterned wafer. The electrical testing may be performed before or after complete semiconductor devices are formed from the electrical elements. In other embodiments, the actual impact of the permissible reticle defects may be analyzed by simulation of the electrical characteristics of electrical elements that will be formed from the patterned wafer. The simulation program may be provided with specific information about the wafer defects that resulted from the permissible reticle defects. The specific information may include results of metrology, inspection, or other analytical testing.

In other embodiments, the method may include analyzing the nuisance defects to determine if the permissible reticle defects were correctly classified, as shown in step 40. For example, the effect that the nuisance defects have on yield of semiconductor devices fabricated on the wafer, which may be determined in step 38, may be used to determine if the reticle defects are actually permissible. In some embodiments, analyzing the nuisance defects to determine the permissibility of the reticle defects may include further metrology or experimental techniques such as high-resolution imaging. In other embodiments, analyzing the nuisance defects to determine the permissibility of the reticle defects may include analyzing or processing data representative of the nuisance defects. For example, modeling may be used to determine the effect that a nuisance defect will have on electrical characteristics of a device formed on the wafer.

If the permissible reticle defects were not correctly classified, the method may include determining if the reticle should be analyzed, reworked, or disposed, as shown in step 42. For example, the reticle may be analyzed to generate information about the incorrectly classified defects such as size, material, phase and transmission characteristics, and proximity to other features on the reticle. In addition, reworking the reticle may include repairing the incorrectly classified defects or removing the incorrectly classified defects from the reticle. The repair process may include chemically assisted laser removal, laser induced shock wave removal, or particle beam assisted repair. An example of a chemically assisted laser removal tool is illustrated in "Chemically Assisted Laser Removal of Photoresist and Particles from Semiconductor Wafers," by Genut et al. of Oramir Semiconductor Equipment Ltd., Israel, presented at the $28^{th}$ Annual Meeting of the Fine Particle Society, Apr. 1-3, 1998, which is incorporated by reference as if fully set forth herein. An example of a laser induced shock wave removal tool is illustrated in U.S. Pat. No. 5,023,424 to Vaught, which is incorporated by reference as if fully set forth herein. A particle beam assisted repair tool may be configured to perform a focused ion beam ("FIB") technique, which is known in the art. Such a particle beam assisted repair tool is commercially available from, for example, Micrion Corporation, Peabody, Mass. Alternatively, reworking the reticle may include cleaning the reticle using a wet or dry cleaning process such as etch or stripping processes. If the incorrectly classified defects are not repairable, the reticle may be disposed. In addition, the reticle may be disposed of if the number of incorrectly classified defects substantially increases the cost of repair. The method shown in FIG. 1 may include any other steps of any other methods described herein.

Figure 4:
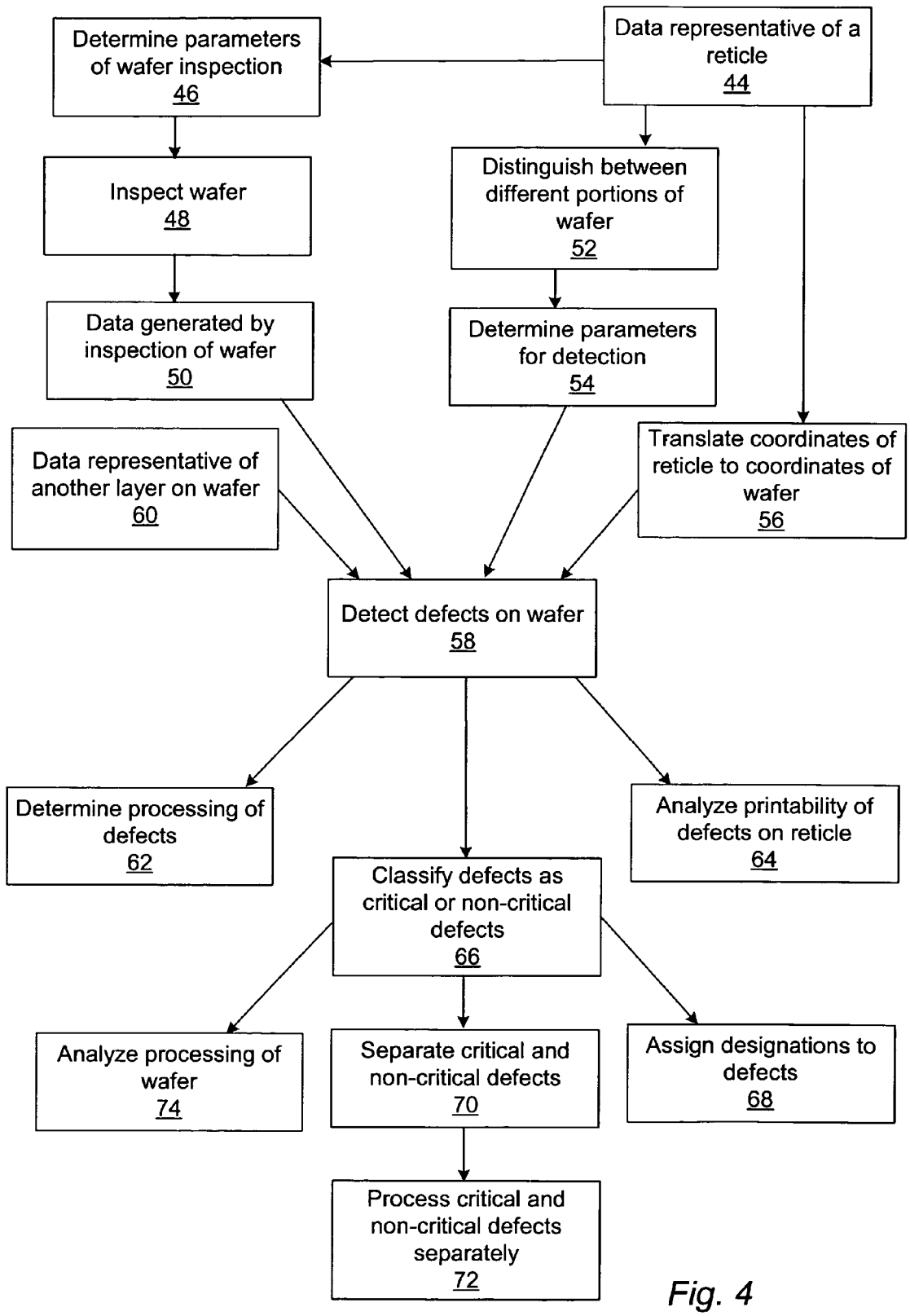
FIG. 4 is a flow chart illustrating an embodiment of a computer-implemented method that includes detecting defects on a wafer by analyzing wafer inspection data in combination with reticle data.

FIG. 4 is a flow chart illustrating a computer-implemented method that includes detecting defects on a wafer by analyzing data generated by inspection of the wafer in combination with data representative of a reticle. The method includes obtaining data representative of the reticle, as shown in step 44. The data representative of the reticle may include macro level information (like the SRAM). The macro level information may include repeating small figures (like cells) amassed into intermediate level figures (like memory pages), which can be brought up together to the macro level. The data representative of the reticle may also be discrete micro features in the logic. Such data may be described in MEBES files, GDSII files or other standard file descriptions of the reticle. The files may include designer intent data as described above such as designations that distinguish between different types of portions of the reticle, features, or portions of features on the reticle.

The method may also include determining parameters of wafer inspection, as shown in step 46. For example, determining parameters of wafer inspection may include identifying different types of portions of the wafer, features, or portions of features on the wafer that correspond to the different types of portions of the reticle, features on the reticle, or portions of features on the reticle based on the data representative of the reticle. In one embodiment, the method may also include distinguishing between different portions of the wafer, as shown in step 52. The different portions of the wafer may be determined based on the data representative of the reticle. In particular, the different portions of the wafer may be determined based on the designations that identify different types of portions of the reticle, which can be correlated to the different portions of the wafer as described herein. For example, the different portions of the reticle may be correlated with areas on the wafer in which these different portions of the reticle are printed. In this manner, different portions of the wafer may be identified as critical or non-critical.

Alternatively, the critical portions of a wafer may be identified based on the criticality associated with different areas of the wafer. The criticality of the different areas of the wafer may be reflected in the designer intent data, which is described further above. In this manner, different portions of the wafer, features, or portions of features on the wafer may be identified as critical or non-critical.

Different parameters of inspection may be associated with the different portions of the wafer, features, or portions of the features on the wafer. For example, the parameters may be selected such that critical portions having different criticalities are inspected with different parameters. The parameters that may be varied may include, but are not limited to, sensitivity and throughput. In one example, if a portion of the wafer is identified as non-critical, this portion of the wafer may be inspected with less sensitivity and higher throughput than a critical portion of the wafer. In another example, if a feature of the wafer is identified as critical, this feature of the wafer may be inspected with higher sensitivity and lower throughput than a non-critical feature of the wafer. In this manner, the parameters of wafer inspection may be varied across the wafer to balance the trade-off between sensitivity and throughput without reducing the accuracy of detection in the critical portions of the wafer. Furthermore, the parameters for inspection of the wafer may be selected such that only the critical portions of the wafer or the portions of the wafer that matter are inspected. In this manner, adequate sensitivity of inspection in the critical portions or the portions that matter may be maintained while the overall throughput of wafer inspection may be increased.

Other parameters of inspection may be varied in a similar manner. Additional parameters that may be varied include the cell size used in bright field array inspection and the point spread function that is used for an array detector such as that included in the AIT systems available from KLA-Tencor. In addition, the parameters of inspection may be varied from wafer to wafer. The method may also include setting the parameters for wafer inspection. Setting the parameters for wafer inspection may include setting up the hardware and/or the software of a wafer inspection system.

As shown in step 48, the wafer may be inspected using the parameters determined in step 46. The wafer may be inspected as described above. In addition, the wafer may be inspected using any of the wafer inspection systems described above. In some embodiments, the wafer inspection may be performed as a process monitor inspection. Such an inspection may be performed during a process or after a process has been performed on a wafer. In addition, such wafer inspection may be carried out automatically by an inspection system that is suitably configured to automatically inspect a wafer during or after a process. The results of the process monitor inspection may be used to analyze the process and may also be used to alter one or more parameters of the process as described herein. Inspection of the wafer produces data generated by inspection of the wafer, as shown in step 50.

In addition, the method may include determining parameters for detection of defects on the wafer, as shown in step 54. Determining parameters for defect detection may be based on the types of the portions of the wafer. The parameters that may be varied may include, for example, a threshold value, a type of algorithm, and/or an inspection method (i.e., array or random). In some embodiments, predetermined thresholds may be associated with different types of portions of the wafer. In this manner, a predetermined threshold may be selected for defect detection in a portion of the wafer based on the type of the portion of the wafer. In one example, if a portion of the wafer is determined to be a critical portion of the wafer based on the reticle information or designer intent data, a lower threshold may be used for this portion of the wafer than the threshold that is used for a non-critical portion of the wafer. In this manner, the sensitivity or method of defect detection may be different in critical and non-critical portions of the wafer. In addition, parameters of detection may be selected such that particular defects may be disregarded even though they are detected. For example, the parameters of detection may be set such that nuisance defects are disregarded even if they are detected. In this manner, the method may include setting parameters for detection in the processor or an image computer for a "difference threshold" to detect defects in different regions (i.e., region based multi-thresholding). As such, nuisance defects on the wafer may not be classified or detected as actual defects on the wafer.

According to another embodiment, information about a reticle or designer intent data and the fault-tolerance of the design may be used to determine which defects may be discarded or classified as nuisance defects. For example, detecting defects may include discarding defects or events in one portion of the wafer that have a lateral dimension smaller than the predetermined threshold associated with this portion of the wafer if other features in this portion of the wafer have a lateral dimension greater than the predetermined threshold. Such defects may be discarded since such defects may not be "killer defects." In a different example, defects in one portion of the wafer may be discarded if an element of a circuit in this portion of the wafer or in a section of the design has a predetermined amount of redundancy and if the defects in this portion of the wafer do not exceed a predetermined density threshold. In one such embodiment, the circuit may be tested upon completion to identify defective redundant elements. In addition, the circuit may be reconfigured to retain only the non-defective redundant elements.

In another example, different algorithms may be used for critical and non-critical portions of the wafer. As such, the parameters of defect detection may be varied across the wafer. In addition, the parameters of defect detection may be varied from wafer to wafer. Other parameters of detection may be varied in a similar manner. For example, the parameters of detection may be selected such that detected defects may be automatically tagged with designations that indicate the portion of the wafer or the type of the portion of the wafer in which the defects are located. Such designations may be used to determine appropriate analysis of the defects such as critical dimension (CD) measurement, scanning electron microscopy analysis, profile analysis, or material analysis. In a similar manner, defects may be automatically assigned designations that directly indicate the type of analysis to be carried out on individual defects.

In one embodiment, correlating different portions of the reticle with different portions of the wafer may include translating coordinates of the reticle to coordinates of the wafer, as shown in step 56. In addition, the method may include translating coordinates of a location of a defect detected on a reticle to coordinates of locations of one or more defects on the wafer. Translating coordinates of the reticle to coordinates of the wafer may be performed as described above.

The method also includes detecting defects on the wafer, as shown in step 58. Detecting the defects on the wafer may be performed using the data generated by inspection of the wafer in combination with the data representative of the reticle. For example, defect detection may be performed using the data generated by inspection of the wafer in combination with the parameters for detection that were determined based on the data representative of the reticle.

The method may also include obtaining data representative of a layer on the wafer, as shown in step 60. The layer may be above or below the level of the wafer, which is being inspected. In one embodiment, defect detection may be performed by analyzing the data generated by inspection of the wafer in combination with the data representative of the reticle and data representative of at least one layer of the wafer above or below the one level of the wafer. This combination of data may also be used to distinguish between critical defects and non-critical defects since features of a device that are above or below a defect may, in some instances, alter the criticality of a defect. For example, a defect that is not critical with respect to the level on which the defect is located may be critical with respect to features that are located above or below the defect in another layer of the wafer.

In one example, if the layer being inspected is used to form the M3 layer of an IC, information about the M2 layer and/or the M4 layer of the IC may be obtained and used for defect detection. In this manner, the method may include utilizing design information for multiple layers of an IC design, including one or more layers above and/or below the layer being currently processed or inspected, to identify critical defects and filter out non-critical defects. For example, the "don't care areas" of a layer of an IC may be determined based on data of another layer of the IC, as described above with respect to FIGS. 3*a*-3*d*. In addition, defects detected in the "don't care areas" may be discarded. Therefore, the criticality of a defect on the wafer may be identified based on the criticality of the portion in which the defect is located and data representative of at least one layer of the wafer above or below the level of the wafer on which the defect is located. In addition, inspection data generated in the "don't care areas" may not be analyzed during defect detection. Alternatively, the "don't care areas" may not be inspected at all.

In some embodiments, the method may also include generating a three-dimensional representation of the defects detected on one level of the wafer. In one such embodiment, the three-dimensional representation may include a three-dimensional representation of other features on the one level of the wafer and/or at least one layer of the wafer above or below this one level. In this manner, the method may include generating and displaying a three-dimensional composite of design layers next to the image of the defect under review. In one embodiment, the layer on which the defect is located may be highlighted, and any relevant design structures on this layer may be identified with some sort of designation.

According to one embodiment, reticle design information or designer intent data may be used as a factor to determine subsequent analysis of a defect. For example, the method may further include determining processing of the defects based on the criticality of the portion in which the defects are located, as shown in step 62. The processing may include additional analytical testing of the defects such as critical dimension (CD) measurements, scanning electron microscopy measurements, or any other metrology, review, or analysis known in the art. In one embodiment, appropriate processing may be determined based on designations assigned to defects during detection as described above. For example, a defect detected using an optical wafer inspection system may be located in a critical area of the wafer as indicated by design information. In this case, the defect may be reviewed using an e-beam review tool. Alternatively, if a defect does not appear to fall in a critical area of the wafer as evident from design information, no further review of the defect may be performed. In this manner, defects identified as critical defects may processed separately from non-critical defects.

In some embodiments, processing the defects may include repairing the defects on the wafer. Repairing defects on the wafer may include simultaneously repairing multiple defects on the wafer using, for example, a cleaning process, an etching process, or a CMP process. Alternatively, repairing defects on the wafer may include repairing the defects one at a time using, for example, a FIB technique. Different types of defects may be subjected to different repair processes. For example, critical defects may be subjected to a more accurate repair process than non-critical defects. In this manner, critical defects and non-critical defects may be separately repaired. In addition, only a portion of all of the defects detected on a wafer may be repaired. For example, critical defects may be repaired while non-critical defects may not be repaired.

In some embodiments, the method may include analyzing the printability of defects detected on the reticle, as shown in step 64. For example, defects on the reticle may be correlated to defects or locations on the wafer based on coordinates of the reticle that are translated to coordinates of the wafer. In addition, the defects or locations on the wafer that correlate to reticle defects may be identified and analyzed to determine how the reticle defects affect the patterned wafer. The printability of permissible reticle defects may be determined to confirm or contradict the permissibility of these defects. In addition, the printability of reticle defects that have not been identified as permissible may also be analyzed in this manner.

The method may also include classifying the defects detected on the wafer as critical defects or non-critical defects, as shown in step 66. In one embodiment, the defects may be classified as critical or non-critical defects based on the portion of the wafer in which the defects are located. In a different embodiment, the defects may be classified as critical or non-critical defects based on the proximity of the defects to a critical or non-critical feature or portion of a feature on the wafer. For example, defects that are located within about 100 nm of a critical feature may be identified as critical, but defects that are located at least about 1000 nm from the critical feature may not be identified as critical. These distances are merely illustrative and may vary greatly depending upon, for example, the type of the feature (i.e., a gate structure or a contact structure) and the size of the defects. In an additional embodiment, defects on the wafer that correlate to permissible defects on the reticle may be identified as non-critical or nuisance defects. In another embodiment, the defects may be classified as critical or non-critical defects based on characteristics of the defects such as phase, transmission, and lateral dimension. The parameters for classification may also be determined based on the portion of the wafer in which the defects are located, or the criticality of the portion of the wafer in which the defects are located. In this manner, the portion of the wafer in which the defect is located may be a factor in assigning a classification to a defect. Classification of the defects may be performed by an image computer or by post-detection software. Classifying the defects may also include assigning other "types" to the defects. For example, classifying the defects may include identifying the defects as scratches, particles, or pits. In some embodiments, classifying the defects may include using a defect source analysis (DSA) algorithm, which is known in the art, or any other algorithm or defect classification method known in the art.

The method may also include assigning designations to the defects, as shown in step 68, if the designations are not already assigned during detection as described above. The designations may be associated with the different portions of the wafer in which the defects are located. In addition, the designations assigned to the defects may be based on the criticality of the portion of the wafer in which the defects are located. The designations may include flags, alphanumeric characters, or any other indicia that can be used to distinguish between different types of defects. Data representative of the defects and the designations assigned to the defects may be stored in a single file. Alternatively, data representative of the defects may be stored in one file, and the designations assigned to the defects may be stored in a different file.

As shown in step 70, the method may include separating the critical defects from the non-critical defects. Separating the critical defects from the non-critical defects may be performed as described above. In some embodiments, the method may include removing data generated by inspection of the wafer at coordinates on the wafer that correspond to a location of a permissible reticle defect from the data generated by the wafer inspection. In addition, the method may include processing the data representative of the critical defects and the non-critical defects separately, as shown in step 72. Processing the data representative of the critical and non-critical defects separately may be performed as described above.

As shown in step 74, the method may further include analyzing a process performed on the wafer based on information about the critical defects and the non-critical defects. Use of designer intent data allows identification of critical defects and filtering out of non-critical defects for the purposes of inspection and review as described above. In one embodiment, however, analyzing and resolving problems with manufacturing processes utilizes both critical and non-critical defect information. In a different embodiment, non-critical defect data may be selectively used for process analysis and troubleshooting. For example, the method may include analyzing the lithography process used to pattern the wafer with the reticle. In addition, the information about the critical defects and the non-critical defects may be used to alter one or more parameters of the lithography process. For example, the method may include altering one or more parameters of the lithography process using a feedback control technique. The one or more parameters of the lithography process may be altered to reduce the number of critical defects that are produced on additional wafers processed using the reticle. The method shown in FIG. 4 may include any other steps of any other methods described herein.

Figure 5:
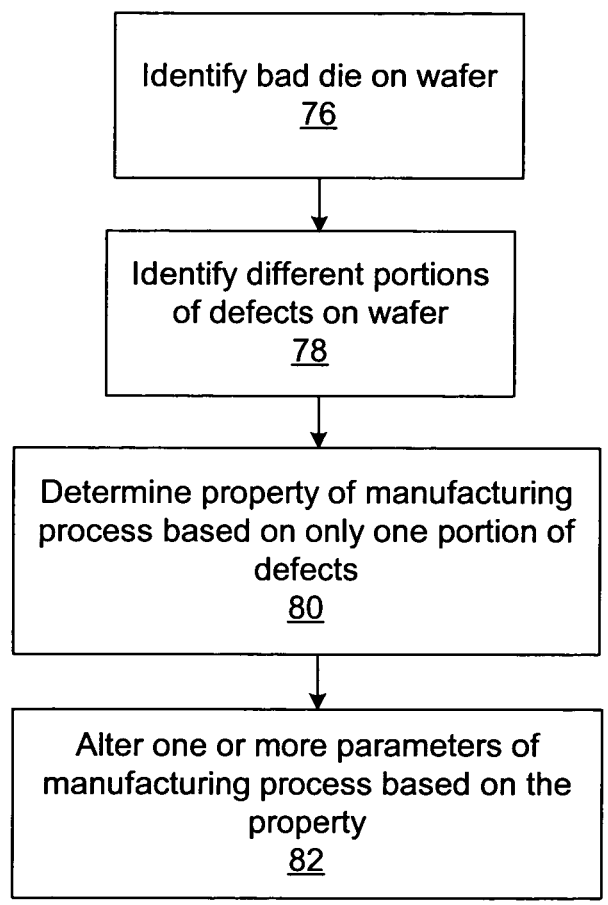
FIG. 5 is a flow chart illustrating an embodiment of a computer-implemented method for selectively using defect information to analyze manufacturing processes.

FIG. 5 is a flow chart illustrating one embodiment of a computer-implemented method for selectively using defect information to analyze manufacturing processes. In current practice, foundries, or IC manufacturing facilities, inspect and review defects occurring on wafers throughout the various IC manufacturing stages to obtain a characteristic defect distribution. This defect distribution may then be used for various purposes including predicting yield and identifying and addressing process limitations. A limitation of this approach is that the defect distribution fails to ignore defects that do not have adverse effects upon the operation of the respective completed IC devices. The computer-implemented method described herein addresses this limitation by refining the defect distribution to provide a more accurate prioritization of defects relevant to the analysis of the manufacturing processes.

According to one embodiment, a computer-implemented method for determining a property of a manufacturing process may include obtaining defect information generated by wafer inspections performed at different times during the manufacturing process. The defect information generated by each inspection may be stored. For example, the defect information may be stored in a memory medium, a database, or a fab database. As shown in FIG. 5, the method also includes identifying bad die on a wafer processed using the manufacturing process, as shown in step 76. Identifying bad die on the wafer may include performing functional testing on the die at the end of the manufacturing process. Alternatively, identifying bad die on the wafer may include performing electrical testing on the die at some point during the manufacturing process. The bad die may contain one or more electrical elements that have functionality outside of a predetermined range.

In addition, the method includes identifying different portions of defects on the wafer, as shown in step 78. In one embodiment, different portions of defects on a wafer may be identified based on data generated by inspection of the wafer in combination with information representative of a design of one or more electrical elements in the bad die. The inspection data may include data generated by multiple inspections of the wafer (i.e., inspection performed at different times during the manufacturing process). One portion of the defects may alter a characteristic of a device formed by the one or more electrical elements such that the characteristic is outside of predetermined limits. For example, design information may be used to efficiently and accurately analyze the defect information for the bad die to identify critical defects while selectively ignoring non-critical defects. The critical defects may be distinguished from the non-critical defects as described herein. In another example, design information may be used to filter out defects identified during wafer inspection or review that have an impact upon the final IC device that is absent or below a certain threshold. The resulting defect distribution provides a more accurate measure of the number and types of defects that are relevant to the manufacturing process.

The method further includes determining a property of the manufacturing process based on one portion of the defects, as shown in step 80. For example, the property of the manufacturing process may be determined based on the critical defects, but not the non-critical defects. In one embodiment, the property of the manufacturing process is a kill ratio of the portion of defects. In another embodiment, the property of the manufacturing process is a yield of the manufacturing process. By removing certain non-critical defects from consideration, one embodiment of the computer-implemented method facilitates a more accurate determination of the "kill ratio" characteristic of the manufacturing process, which in turn enables a more precise estimation of the characteristic yield.

The method may also include altering one or more parameters of the manufacturing process based on the property of the manufacturing process, as shown in step 82. One or more parameters of the manufacturing process may be altered using a feedback control technique. Since the parameters may be determined based on a more accurate determination of the kill ratio or yield of the manufacturing process, the performance of the manufacturing process using the altered parameters may be significantly improved. The manufacturing process may be analyzed and altered in such a manner a number of times to reduce the kill ratio and to increase the yield of the manufacturing process even further. The method shown in FIG. 5 may include any other steps of any other methods described herein.

Figure 6:
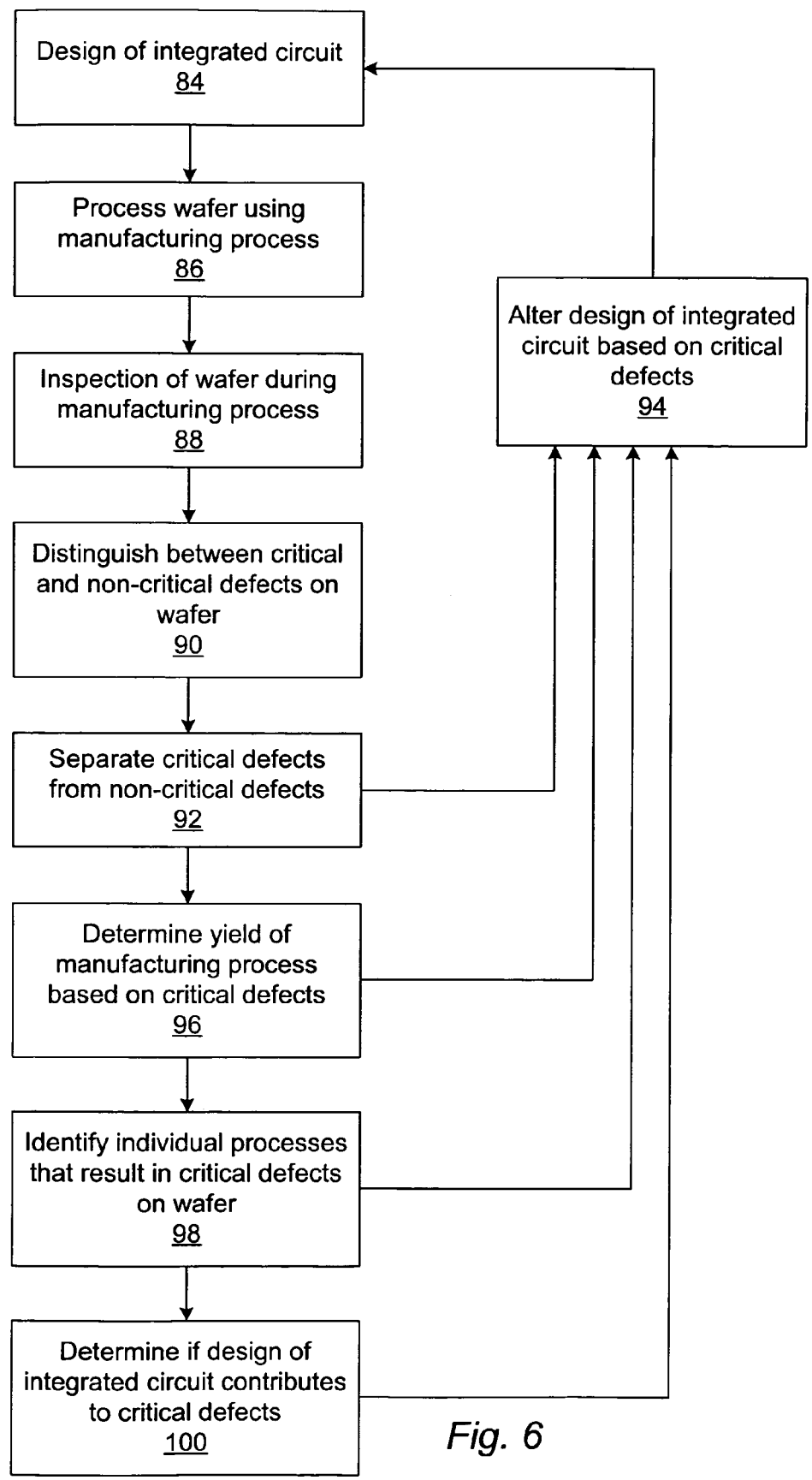
FIG. 6 is a flow chart illustrating an embodiment of a computer-implemented method for altering a design of an IC based on a selected portion of defects detected on a wafer.

FIG. 6 is a flow chart illustrating a computer-implemented method that includes altering a design of an IC based on data generated by inspection of a wafer performed during a manufacturing process. According to one embodiment, the method may be used for enhancing the design process of an IC device based on defect information obtained during the manufacturing process for the IC device. The defect information may be analyzed in terms of the design information. The method provides a feedback method in which the design and manufacturing phases of an IC device are progressively optimized based on design information.

Currently, defect inspection and review during the manufacturing phase of an IC device produces large amounts of defect-related data for each manufacturing process. Foundries generally limit use of this defect data to immediate troubleshooting of process issues with the goal of eliminating the defects in subsequent batches of IC devices. Depending on various constraining limitations imposed by the characteristics of the IC devices being manufactured and by the processes employed during the manufacturing phase, however, further improvement of the processes may become difficult and expensive at some point, with a reduced impact on defect reduction. For example, one or more processes performed during the manufacturing phase of a microprocessor may be unable to reliably meet critical dimension requirements.

The computer-implemented method includes designing an IC, as shown in step 84. The IC may be designed using any method known in the art. The method also includes processing a wafer using a manufacturing process, as shown in step 86. The manufacturing process may include a number of individual processes such as deposition, lithography, etch, chemical-mechanical planarization, plating, ion implantation, cleaning, and epitaxy. In addition, the manufacturing process may include performing some of the individual processes more than once. As shown in step 88, the method includes inspecting the wafer during the manufacturing process. The wafer may be inspected multiple times during the manufacturing process. For example, the wafer may be inspected after a lithography process, after an etch process, after a chemical-mechanical planarization process, and/or after a cleaning process. In some cases, the wafer may be inspected during one or more of the individual processes.

Critical and non-critical defects may be detected on a wafer during the inspection of the wafer. As shown in step 90, the method may include distinguishing between critical and non-critical defects on the wafer based on the IC design. For example, the IC design may include designations that may indicate different portions of the design. The designations may be further configured as described above. In one embodiment, the criticality of the defects may be determined based on the portion of the design in which the defect is located. In another embodiment, the critical defects may include defects that may alter one or more characteristics of the IC. In contrast, the non-critical defects may include defects that will not substantially alter one or more characteristics of the IC.

In some embodiments, the method may include separating critical defects from non-critical defects, as shown in step 92. In this manner, the critical defects may be easily processed separately from the non-critical defects. The critical and non-critical defects may be separated as described above. In addition, the method includes altering the design of the IC based on the defects detected on the wafer, a substantial portion of which include critical defects, as shown in step 94. In this manner, using the design information, the method selectively ignores defects that are not critical to the functionality of the completed IC device thereby reducing or eliminating the limitations of the currently used methods. As shown in FIG. 6, altering the design of the IC may be performed using a feedback control technique.

In one embodiment, the design of the IC may be altered to reduce the number of critical defects that are formed during the manufacturing process. In another embodiment, the method may include determining a yield of the manufacturing process based on the critical defects, as shown in step 96. In such an embodiment, the design of the IC may be altered to increase the yield of the manufacturing process. In some embodiments, the method may include identifying one or more individual processes of the manufacturing process that result in at least some of the critical defects being formed on the wafer, as shown in step 98. Therefore, using the design information, the method permits a more accurate identification of the truly-limiting processes during the manufacturing phase.

According to one embodiment, once these limiting processes are identified with an improved degree of confidence, information about particular characteristics of the design that tend to induce failure of the limiting processes is used to refine the design of the IC device. In this manner, the design of the IC may be altered in response to the individual processes that produce critical defects on the wafer. In one such embodiment, the method may also include determining if the design of the IC contributes to the formation of the critical defects, as shown in step 100. In addition, the design of the IC may be altered to reduce a number of the critical defects that are formed during the individual processes.

An enhanced design that reduces critical defects during the manufacturing phase could provide enhanced sensitivity and throughput during subsequent inspection and review. This feedback method for enhancing the IC design phase may be performed more than one time to progressively improve the yield of the manufacturing phase. In an additional embodiment, the manufacturing process may be altered based on the information about defects that were detected on the wafer. The method shown in FIG. 6 may include any other steps of any other methods described herein.

Figure 7:
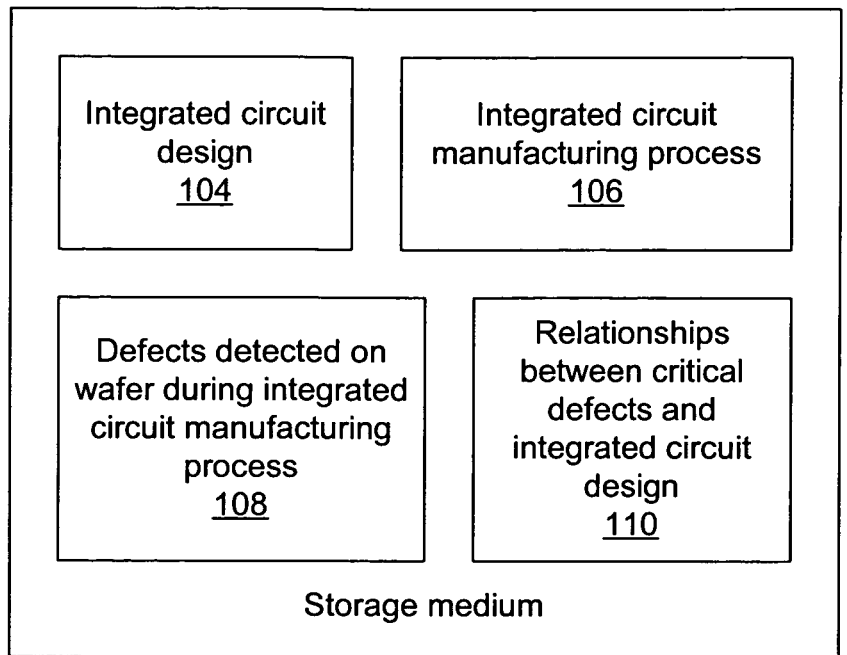
FIG. 7 is a schematic diagram illustrating an embodiment of a storage medium that can be used to alter an IC design to enhance the manufacturability of the IC design.

FIG. 7 is a schematic diagram illustrating storage medium 102. In one embodiment, the storage medium may be a database. In another embodiment, the storage medium may include any medium suitable for storage of data known in the art. Storage medium 102 includes data representative of an IC design 104. Storage medium 102 also includes data representative of an IC manufacturing process 106. In addition, storage medium 102 includes defect data 108 representative of defects detected on a wafer during the IC manufacturing process. The defect data may be filtered such that a substantial portion of the defects includes critical defects that can alter one or more characteristics of the IC. In particular, the defect information may be filtered using design information to exclude non-critical defects that have no impact or only a limited impact on the functionality of the completed IC device.

In some embodiments, the storage medium may also include data representative of relationships between the critical defects and the IC design 110. In particular, the relationships may be relationships between IC design characteristics and defects that may occur during the manufacturing phase in connection with various manufacturing processes. In one embodiment, the storage medium can be used to alter the IC design based on the data representative of the IC design 104, the data representative of the IC manufacturing process 106, and defect data 108. In some embodiments, the storage medium may be used to alter the IC design using a relationship between the IC design characteristics and the defects. Therefore, the storage medium may be used during the design phase to enhance the fitness of the design for manufacturability. In addition, the storage medium illustrated in FIG. 7 may be used to carry out the method illustrated in FIG. 6.

Figure 8:
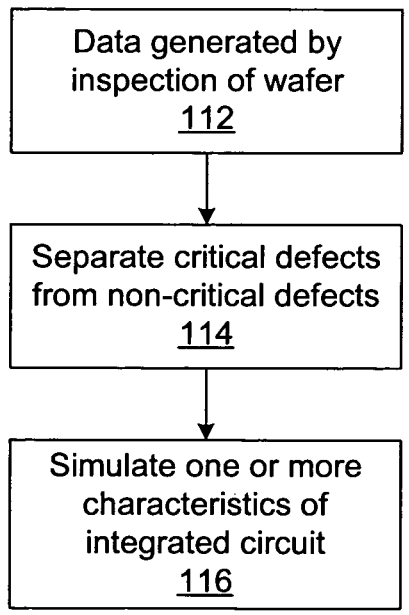
FIG. 8 is a flow chart illustrating an embodiment of a computer-implemented method for simulating one or more characteristics of an IC based on defect data.

FIG. 8 is a flow chart illustrating an embodiment of a computer-implemented method that includes simulating one or more characteristics of an IC based on defect data generated by inspection of a wafer during a manufacturing process. A substantial portion of the defects includes critical defects that can alter one or more characteristics of the IC. In some embodiments, the method may be used to simulate the impact of the defects on the functionality of a complete IC device. In contrast, currently, IC design tools simulate the performance of an IC design without using manufacturing process information. Instead, such simulations generally focus on non-process-related relationships such as the relationship between design rules and timing. In addition, tools for simulation of the impact of defects on fully-manufactured IC devices currently only take into account limited information regarding the defects. Consequently, the ability to predict the impact of the defects on an IC design is relatively inaccurate and unreliable. In contrast, the method described herein provides an enhanced method for simulation of the performance of an IC design by taking into account manufacturing process information. In addition, the method described herein addresses the limitations of other simulation methods by utilizing comprehensive defect information while simulating the impact of defects on the functionality of a final, completed IC device. The manufacturing process information and the comprehensive defect information may be obtained using IC design information.

As shown in step 112, the method may include generating data by inspecting a wafer. The wafer may be inspected at any time during a manufacturing process. In alternative embodiments, the method may include obtaining data generated by inspection of a wafer as described above. In one embodiment, the data may be generated by inspection and review performed during various stages of the manufacturing process of the IC device. In some embodiments, the information about the defects may include coordinates of defect locations on the wafer and three-dimensional defect profiles. The information about the defects may include, however, any other information about the defects that may be generated during inspection or review.

The method also includes separating critical defects from non-critical defects, as shown in step 114. Critical defects may be separated from non-critical defects using designer intent data as described herein. For example, the method may include distinguishing between critical defects and non-critical defects detected during the inspection based on the design of the IC. The non-critical defects may be identified as those defects that will not substantially alter the one or more characteristics of the IC (i.e., defects that are not critical to the performance of the IC device). In this manner, information about the yield and performance of various processes employed during the manufacturing phase is obtained by selectively ignoring defects that, based on design information, are determined to be not critical to the performance of the completed IC device.

The method includes simulating one or more characteristics of an IC based on the defect data, as shown in step 116. In some embodiments, the information about the various manufacturing processes obtained above may also be used to simulate one or more characteristics of the IC. The information about the various processes obtained above may be used to more accurately simulate the performance of the design of the IC device. In addition, such preprocessing of the defect information ensures that the simulation can be performed more efficiently, faster, and using less computational resources. In a particular implementation, the defect data used for the simulation includes defect coordinates and a three-dimensional defect profile. The one or more characteristics of the IC may include, but are not limited to, voltage drops, timing slow-downs, partial device failure, and total device failure. The method shown in FIG. 8 may include any other steps of any other methods described herein.

Figure 9:
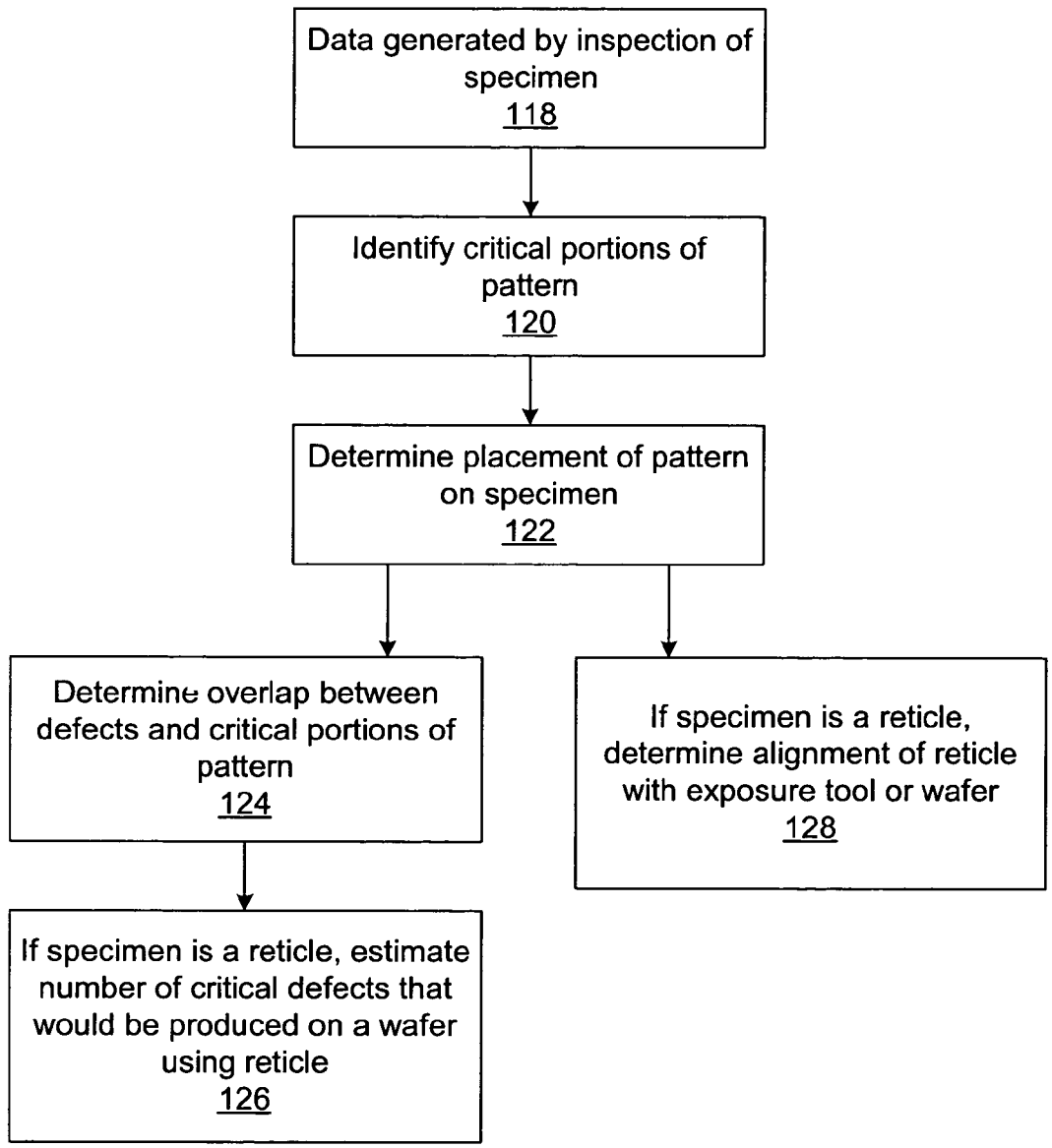
FIG. 9 is a flow chart illustrating an embodiment of a computer-implemented method that includes determining placement of a pattern on a specimen based on defect data.

FIG. 9 is a flow chart illustrating an embodiment of a computer-implemented method that includes determining placement of a pattern on a specimen based on defect data. In one embodiment, the method includes using design information to selectively match a design pattern to a blank medium exhibiting defects. In an embodiment, the specimen may be a blank reticle substrate. In an alternative embodiment, the specimen may be a wafer. The wafer may be a blank wafer or a wafer prior to having a patterned layer formed thereon. The wafer may, however, have other patterned layers previously formed thereon. Such previously patterned layers may be formed underneath the layer about to be patterned. However, the computer-implemented method described herein may be applied to most cases where a pattern is imprinted or otherwise impressed upon a medium or specimen that may exhibit defects, including any such specimen known in arts other than the semiconductor industry.

As shown in step 118, the method may include generating data by inspecting a specimen. In different embodiments, the method may include obtaining the data generated by inspection of a specimen as described above. The method may also include identifying critical portions of the pattern, as shown in step 120. In some embodiments, identifying critical portions of the pattern may be based on design information as described herein. In alternative embodiments, the method may include identifying critical portions of the pattern without such design information. For example, alignment of the pattern with a blank reticle substrate may be performed without using the design information.

In addition, the method may include determining placement of the pattern on the specimen, as shown in step 122. Determining the placement of the pattern may include laterally translating the pattern, rotating the pattern, scaling the pattern, or any combination thereof. Laterally translating the pattern may include laterally translating the pattern in the x direction and/or the y direction. In one embodiment, determining the placement of the pattern may include selecting the placement of the pattern such that a substantial portion of the defects on the specimen does not overlap with the pattern. In some embodiments, determining the placement of the pattern may include determining the placement of the critical portions of the pattern with respect to locations of defects on the specimen. For example, determining the placement of the pattern may include selecting the placement of the pattern such that a substantial portion of defects on the specimen does not overlap with critical portions of the pattern. In one particular example, inspection of a blank reticle substrate identifies a number of defects on the substrate. The design pattern to be printed on the reticle substrate may then be aligned and printed on the reticle substrate such that the defects on the blank reticle substrate do not overlap any critical areas of the design pattern. In an additional embodiment, determining the placement of the pattern may include selecting the placement of the pattern such that an amount of overlap between defects on the specimen and critical portions of the pattern is below a predetermined threshold. In this manner, a certain degree of overlap between defects on the specimen and critical areas on the specimen may be tolerated, and the design pattern may be printed such that the degree of overlap is below a certain threshold.

In some embodiments, the method may also include determining overlap between defects on the specimen and critical portions of the pattern, as shown in step 124. In further embodiments, if the specimen is a blank reticle substrate, the method may include determining an amount of overlap between defects on the reticle and critical portions of the pattern. The degree of overlap between defects on the blank reticle and critical areas of the design pattern may be an indicator of the expected number of critical defects that would be produced by using the patterned reticle to expose a wafer. Therefore, such an embodiment may also include estimating the number of critical defects that may be produced on a wafer using the reticle, as shown in step 126. In another embodiment, if the specimen is a blank reticle substrate, the method may include determining alignment of the reticle with an exposure tool and/or wafer based on the placement of the pattern with respect to a coordinate system, as shown in step 128. For example, information regarding the displacement of the design pattern with respect to nominal coordinates may be stored and may be subsequently used to properly align the reticle with the stepper and/or the wafer. In a similar manner, a reticle may be selectively aligned with a wafer exhibiting defects during wafer patterning.

The computer-implemented method illustrated in FIG. 9 provides several advantages including, but not limited to, the ability to tolerate defects on blank reticle substrates and wafers, cost savings by reducing, and even eliminating, the need to replace or repair blank reticle substrates and wafers, and time savings by reducing, and even eliminating, processing delays associated with rejection and replacement of the defective blank reticle substrates or wafers. The method shown in FIG. 9 may include any other steps of any other methods described herein.

Figure 10:
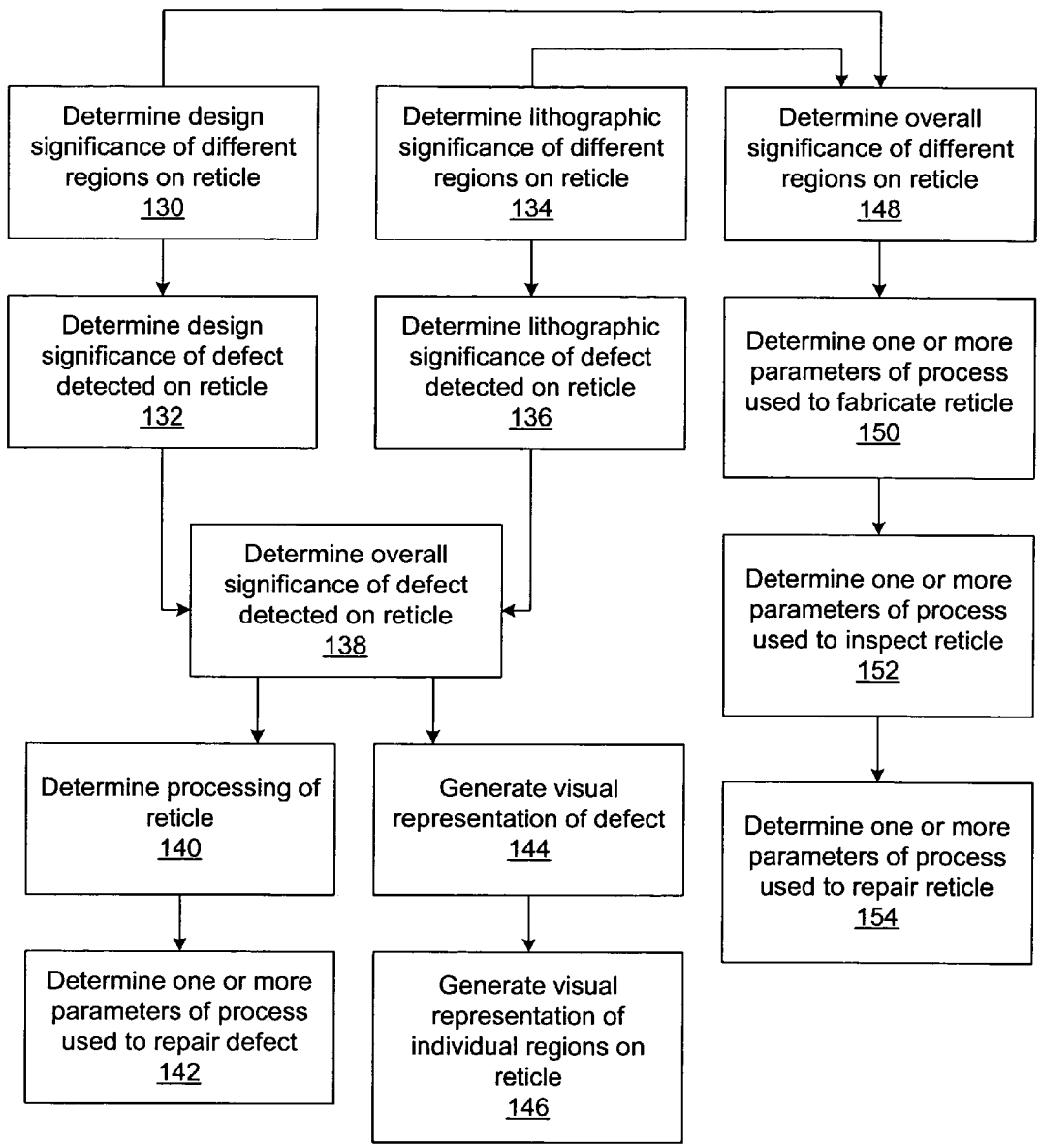
FIG. 10 is a flow chart illustrating an embodiment of a computer-implemented method for determining the significance of a defect.

FIG. 10 is a flow chart illustrating an embodiment of a computer-implemented method for determining the significance of a defect. Reticles are used as the master patterns in the manufacture of semiconductor devices. Automated inspections of reticles are standard steps in the production of these semiconductor devices. The inspections are used to detect defects on the reticles, which may then be rejected, repaired, cleaned, or passed based on defect disposition criteria. The inspections are critical because even one significant defect on a reticle can cause every semiconductor device manufactured with the reticle to fail or be flawed in some way. As more complex semiconductor designs are developed, the designs result in more complex reticles and more complex lithographic techniques. Smaller design sizes combined with increasing complexities have resulted in increasing difficulty in detecting and accurately dispositioning reticle defects. For example, there can be a substantially non-linear relationship between what is on the reticle (design or defect) to what resulting pattern is generated on the wafer.

Methods for determining the printability of a defect have been developed. For example, a system and a method for determining reticle defect printability are illustrated in U.S. Pat. No. 6,076,465 to Vacca et al. and U.S. Pat. No. 6,381,358 to Vacca et al. and U.S. patent application Ser. No. 10/074,857 entitled "System and Method for Determining Reticle Defect Printability" by Vacca et al., filed on Feb. 11, 2002, which are incorporated by reference as if fully set forth herein. Examples of designer intent data and methods of use for reticle inspection are illustrated in U.S. Pat. No. 6,529,621 to Glasser et al. and PCT Application No. WO 00/36525 by Glasser et al., which are incorporated by reference as if fully set forth herein.

The computer-implemented method described herein provides a method for determining the significance or potential significance of a defect on a reticle. This method may utilize a reticle pattern generation system or a reticle inspection system. As shown in step 130, the method includes determining the design significance of different regions on a reticle. In some embodiments, the regions of greater or lesser design significance on a reticle may be determined by an automatic computer program with information about the reticle and the context of the full reticle design. Determining the design significance of the different regions on the reticle may or may not be performed during a pre-processing step carried out before inspection. Alternatively, determining the design significance of the different regions may be performed during inspection or during a post-processing step carried out after inspection.

The method also includes determining the design significance of a defect detected on the reticle, as shown in step 132. The design significance is a measure of how the defect impacts the design of the reticle. The design significance of the defect may be determined based on the design significance of the region on the reticle in which the defect is located. Alternatively, the design significance of the defect may be determined by comparing data representative of the defect to a threshold and determining that the defect has design significance if the data is greater than the threshold. In some embodiments, the data representative of the defect may include phase and/or transmittance of the defect, a lateral dimension of the defect, or a distance between the defect and other features on the reticle. In one embodiment, the threshold may vary depending on the location of the defect on the reticle. Therefore, each defect or location on the reticle may have a threshold above which a defect may be determined to have design significance. For example, the threshold may have a lower value in a region of the reticle having a greater design significance than the value of the threshold in a region of the reticle having a lower design significance.

The method also includes determining the lithographic significance of different regions on the reticle, as shown in step 134. For example, information about the lithographic process in which this reticle will be used may be obtained. In one embodiment, the information about the lithographic process may be obtained from a fab database. In another embodiment, the information about the lithographic process may be obtained from simulation software that may be used to determine a process window for the lithographic process. In a different embodiment, the information about the lithographic process may be obtained from experimental results obtained using a process window characterization (PWC) reticle. Regions of greater or lesser lithographic criticality on a reticle may, in some embodiments, be determined by an automatic computer program with information about the design of the reticle and the lithographic process. Determining the lithographic significance of different regions on the reticle may be performed during a pre-processing step carried out before reticle inspection, during reticle inspection, and/or during a post-processing step carried out after reticle inspection.

The method further includes determining the lithographic significance of a defect detected on the reticle, as shown in step 136. The lithographic significance is a measure of how the defect impacts a wafer patterned by a lithography process that uses the reticle. The lithographic significance of the defect may be determined based on the lithographic significance of the region on the reticle in which the defect is located. Alternatively, the lithographic significance of the defect may be determined by comparing data representative of the defect to a threshold and determining that the defect has lithographic significance if the data is greater than the threshold. The data representative of the defect may include any of the data described above. In one embodiment, the threshold may vary depending on the location of the defect on the reticle. In this manner, each defect or location on the reticle may have a threshold above which a defect may be determined to have lithographic significance. For example, the threshold may have a lower value in a region of the reticle having a greater lithographic significance than the value of the threshold in a region of the reticle having a lower lithographic significance.

As shown in step 138, the method includes determining an overall significance of a defect detected on the reticle. The overall significance of the defect may be determined based on the design significance and the lithographic significance of the defect. Therefore, the method may be used to determine the overall significance of a defect by determining the design significance of the defect in a particular location on the reticle combined with the lithographic significance of the defect in a particular location on the wafer. The overall significance of the defect may be selected from one of the following 4 categories: lithographically and design significant, lithographically significant only, design significant only, and not significant. Each defect may be assigned to one of the 4 categories.

Figure 11:
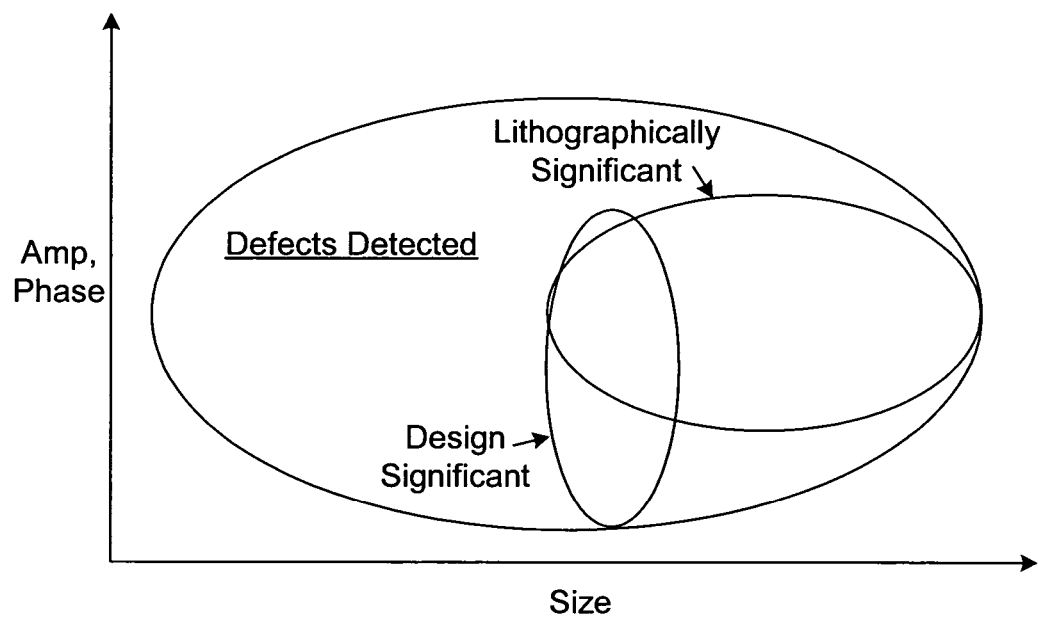
FIG. 11 is a conceptual diagram illustrating how defects on a reticle may fall into categories of differing significance.

The chart shown in FIG. 11 is a conceptual diagram illustrating how defects may fall into each of these categories. As shown in FIG. 11, the significance of defects may vary as a function of amplitude (or transmittance) and phase as well as size. The significance of the defects, however, may also vary as a function of other characteristics of the defects and the reticle. For example, the significance of the defects may vary as a function of the distance between the defects and other features on the reticle. As further shown in FIG. 11, different defects detected on a reticle may have design significance or lithographic significance. Of all of the defects that have some kind of significance, an even smaller portion of these defects have both design and lithographic significance. Applying both criteria for significance to defects allows the semiconductor manufacturing process to be analyzed or changed based on the most significant regions or defects on a reticle while retaining information (if desired) about the less significant regions or defects.

In some embodiments, the method may include determining processing of the reticle, as shown in step 140 of FIG. 10. In one such embodiment, the processing of the reticle may be determined based on the design, lithographic, and/or overall significance of individual defects on the reticle. Processing of the reticle may include, but is not limited to, rejecting the reticle, repairing the reticle, and/or cleaning the reticle. By combining the information about both types of significance, it may be possible to reduce or eliminate the necessity to reject, repair, or clean certain reticles.

In additional embodiments, the method may include determining one or more parameters of a process used to repair a defect on the reticle, as shown in step 142. For example, one or more parameters of a process used to repair a defect may be determined based on the design, lithographic, and/or overall significance of the defect. In this manner, one or more of the parameters used to repair different defects on the reticle may be different. For example, a defect that has a higher overall significance may be repaired using a process that has a higher accuracy than the process that is used to repair a defect that has a lower overall significance. The repair process may include any of the repair processes described herein and any other repair process known in the art. Determining processing of the reticle or one or more parameters of a process used to repair a defect on the reticle may be performed in an automated manner thereby reducing, or even eliminating, the need for a person to make the decision on dispositioning defects.

In one embodiment, the method may include generating a visual representation of a defect detected on the reticle, as shown in step 144. The visual representation may include one or more designations assigned to the defect, which indicate the design, lithographic, and/or overall significance of the defect. The visual representation may also include a two-dimensional visual representation of the defect, a three-dimensional visual representation of the defect, a two-dimensional map of a region on the reticle in which the defect is located, or a two-dimensional map of the reticle on which the defect is located. In addition, the visual representation of the defect may be overlaid with other data representative of the defect, the region of the reticle in which the defect is located, or the reticle on which the defect is located. For example, the visual representation of the defect may include visual representations of other features on the reticle that may be proximate to the defect and, in some cases, designations assigned to the features, which may or may not indicate the design, lithographic, and/or overall significance of these features. In some embodiments, the method may include generating a visual representation of individual regions on the reticle, as shown in step 146. In one such embodiment, the visual representation may include designations assigned to the individual regions indicating the design, lithographic, and/or overall significance of the individual regions. This visual representation may be further configured as described above. In this manner, the method may be used to indicate regions or defects of greater or lesser significance when presenting results to a user. Furthermore, critical design regions and/or critical lithographic regions may be indicated as well as regions of high mask error enhancement factor (MEEF).

In an embodiment, the method may include determining an overall significance of different regions on the reticle, as shown in step 148. The overall significance of the different regions on the reticle may be determined based on the design significance and the lithographic significance of the different regions on the reticle. In some embodiments, the overall significance of the different regions on the reticle may be used to determine the overall significance of a defect on the reticle. For example, a defect on the reticle may be assigned the same overall significance as the region on the reticle in which the defect is located. In such embodiments, the design significance and the lithographic significance of the defect may or may not be determined as described above.

By combining the information about both types of significance, the method can be used to improve the yield, cycle time, efficiency, and other aspects of the semiconductor manufacturing process concerning reticles. In particular, it may be possible to improve the pattern generation process by adjusting system parameters based on the significance of a particular location on a reticle. In one embodiment, the method may include determining one or more parameters of a process used to fabricate the reticle, as shown in step 150. The parameters of the process may be determined based on the design, lithographic, and/or overall significance of different regions of the reticle. In some embodiments, the parameters of the process may be determined independently for different regions on the reticle. In this manner, one or more of the parameters of the process may be different for more than one region on the reticle. As such, the parameters of the process may vary independently across the reticle. For example, the parameters of the reticle fabrication process in a region of the reticle having a higher overall significance than another region on the reticle may be selected such that the region having the higher overall significance is processed with greater writing fidelity than the other region. Rules for fabrication process tool parameters in regions of varying significance may be manually set by a user or may be set automatically by a processor configured to perform the method shown in FIG. 10. Examples of reticle fabrication processes include pattern generation, etch, cleaning, and any other reticle fabrication process known in the art.

In a further embodiment, the method may include determining one or more parameters of a process used to inspect the reticle, as shown in step 152. The parameters that may be altered may be parameters of an inspection tool configured to perform reticle inspection. The parameters of the inspection process may be determined as described above. As such, the parameters of the inspection process may vary independently from region to region across the reticle. For example, the parameters of the inspection process may be selected to have higher sensitivity in one region than the sensitivity used to inspect other regions on the reticle. In particular, the defect sensitivity of reticle inspection may be the greatest in the most lithographically and design significant regions of the reticle. The increased sensitivity in the most lithographically and design significant regions of the reticle may increase the yield or performance of semiconductor devices fabricated using such a reticle. The inspection process for the reticle may be any suitable inspection process known in the art such as inspection based on light transmitted and/or reflected by the reticle and aerial imaging based inspection.

For processing of data generated by reticle inspection, defect detection in any of several modes (die:die detection, die:database inspection, or any other mode known in the art) may be performed. One or more parameters of the inspection data processing may also be varied based on the significance of a particular region or defect on the reticle. The one or more parameters of data processing that may be altered include a value of a threshold or an algorithm that is used for defect detection. In a similar manner, the parameters of a process used to review defects on the reticle may be determined as described above. Rules for inspection system and/or review system parameters in regions of varying significance may be set manually by a user or may be set automatically by a processor configured to perform the method described herein.

In another embodiment, the method may include determining one or more parameters of a process used to repair the reticle, as shown in step 154. The parameters of the repair process may be determined as described above. As such, the parameters of the repair process may vary independently from region to region across the reticle. For example, the parameters of the repair process may be selected to have higher accuracy in one region than the accuracy used to repair other regions on the reticle. Rules for repair tool parameters in regions of varying significance may be set manually by a user or may be set automatically by a processor configured to perform the method described herein. The repair process for the reticle may be any suitable repair process known in the art such as chemically assisted laser removal, laser induced shock wave removal, particle beam assisted repair, or cleaning the reticle using a wet or dry cleaning process such as etch or stripping processes, which are described in further detail above. The method shown in FIG. 10 may include any steps of any other methods described herein.

Program instructions implementing methods such as those described above may be transmitted over or stored on a carrier medium. The program instructions may be executable on a computer system to perform any of the computer-implemented methods described herein. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape. One or more data structures and/or rules databases may similarly be transmitted over or stored upon such a carrier medium.

A system configured to perform any of the computer-implemented methods described herein may include a processor. The processor may be configured to execute program instructions for performing one or more of the computer-implemented methods described herein. The processor may be any suitable processor known in the art. In one example, the processor may be an image computer. In another example, the processor may be any suitable microprocessor known in the art.

The system and the processor may be configured in various ways. In one embodiment, the system may be configured as a stand-alone system. In this manner, the system may not be coupled to another system or tool except by a transmission medium. For example, the processor of the system may be coupled to a processor of a reticle and/or wafer inspection system by a transmission medium. One such configuration is shown in FIG. 2. The transmission medium may include any of the transmission mediums described above. In one embodiment, the system may be a stand-alone system that is coupled to an inspection system, a defect review system, a reticle fabrication tool, and/or a repair tool. In some embodiments, the system may be coupled to more than one system and/or more than one tool. In another embodiment, the system may be a stand-alone system that is coupled to a fab database. In an additional embodiment, the system may be coupled to a fab database in addition to another system and/or tool.

In other embodiments, the processor of the system may be incorporated into an inspection system, a defect review system, a reticle fabrication tool, or a repair tool. For example, a processor of an inspection system may be configured to perform one or more of the computer-implemented methods described above in addition to other standard functions of such a processor. In the case of an inspection system, examples of such standard functions may include receiving and processing signals generated by detectors of the inspection system and calibrating the inspection system.

In any of the above embodiments, the processor may be configured to control one or more parameters of the inspection system, the defect review system, the reticle fabrication tool, and/or the repair tool. For example, the processor may be configured to alter one or more parameters of the inspection system, the defect review system, the reticle fabrication tool, and/or the repair tool according to any of the above embodiments. In another embodiment, the processor may be configured to send the altered parameters and instructions to change the parameters to a processor of an inspection system, a defect review system, a reticle fabrication tool, and/or a repair tool.

Further modifications and alternative embodiments of various aspects of the invention may be apparent to those skilled in the art in view of this description. For example, methods and systems for inspection of wafers and reticles using designer intent data are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method, comprising identifying nuisance defects on a wafer based on inspection data produced by inspection of a reticle, wherein said identifying is performed using a computer processor, and wherein the reticle is used to form a pattern on the wafer prior to inspection of the wafer.

2. The method of claim 1, wherein the nuisance defects are formed on the wafer as a result of defects on the reticle that were determined to be permissible reticle defects.

3. The method of claim 1, wherein the nuisance defects are formed on the wafer as a result of defects on the reticle that were determined to he permissible reticle defects based on designer intent data.

4. The method of claim 1, further comprising separating the nuisance defects from actual defects on the wafer and processing data representative of the actual defects.

5. The method of claim 1, further comprising transmitting the inspection data from an inspection system used to perform the inspection of the reticle to the processor configured to perform the method.

6. The method of claim 1, further comprising transmitting the inspection data from a fab database to the processor configured to perform the method.

7. The method of claim 6, wherein said transmitting comprises sending coordinates of defects detected on the reticle and images of the defects.

8. The method of claim 1, wherein the inspection data comprises coordinates of a location of a defect on the reticle, the method further comprising translating the coordinates to coordinates of locations of one or more of the nuisance defects on the wafer.

9. The method of claim 1, further comprising determining if the nuisance detects will affect yield of semiconductor devices, wherein the semiconductor devices will be formed on the wafer.

10. The method of claim 1, wherein the nuisance defects are formed on the wafer as a result of defects on the reticle that were determined to be permissible reticle defects, the method further comprising analyzing the nuisance defects to determine if the permissible reticle defects were correctly classified.

11. The method of claim 10, wherein if the permissible reticle defects were not correctly classified, the method further comprising determining if the reticle should be analyzed, reworked, or disposed.

12. The method of claim 1, further comprising generating a two-dimensional map of the wafer, wherein the nuisance defects are distinguished from other defects in the map by one or more different designations.

13. A computer-implemented method, comprising identifying locations on a wafer in which nuisance defects will be formed based on inspection data produced by inspection of a reticle, wherein said identiing is performed using a computer processor.

14. The method of claim 13, further comprising selecting one or more parameters for wafer inspection such that the locations are not inspected.

15. The method of claim 13, further comprising selecting one or more parameters for wafer defect review such that the nuisance defects are not reviewed.

16. The method of claim 13, further comprising selecting one or more parameters for wafer defect analysis such that the nuisance defects are not analyzed.

17. A computer-implemented method, comprising:
identifying critical portions of a wafer based on criticality associated with different areas of the wafer; and
selecting parameters for inspection of the wafer such that only the critical portions of the wafer are inspected, wherein said identifying and said selecting are performed using a computer processor.

18. The method of claim 17, wherein the parameters are selected such that the critical portions having different criticalities are inspected with different parameters.

19. The method of claim 17, further comprising translating coordinates of a location of a detect detected on a reticle to coordinates of locations of one or more detects on the wafer and analyzing the printability of the detect detected on the reticle.

20. The method of claim 17, further comprising translating coordinates of a location. of a defect detected on a reticle to coordinates of locations of one or more defects on the wafer and removing inspection data at the coordinates on the wafer from wafer inspection data.

21. The method of claim 17, further comprising generating one or more two-dimensional maps illustrating the critical portions of the wafer.

22. The method of claim 17, wherein said selecting comprises selecting the parameters such that nuisance defects on the wafer are not classified as actual defects.

23. The method of claim 17, further comprising assigning a designation to a defect on the wafer based on the criticality of the critical portion in which the defect is located.

24. The method of claim 17, further comprising determining processing of a defect on the wafer based on the criticality of the critical portion in which the defect is located.

25. The method of claim 17, further comprising setting one or more parameters for classification of defects on the wafer based on the criticality of the critical portions.

26. The method of claim 17, further comprising classifying defects on the wafer as critical defects or non-critical defects and analyzing a process performed on the wafer based on the critical defects and the non-critical defects.

27. The method of claim 17, further comprising classifying defects on the wafer as critical defects or non-critical defects and processing the critical defects separately from the non-critical defects.

28. The method of claim 17, further comprising discarding inspection data representing defects in one of the critical portions if the defects have a lateral dimension smaller than a predetermined threshold and if other features in the one portion have a lateral dimension greater than the predetermined threshold.

29. The method of claim 17, further comprising discarding inspection data representing defects in one of the critical portions if an element of a circuit in the one portion has a predetermined amount of redundancy and if defects in the one portion do not exceed a predetermined density threshold.

30. The method of claim 17, wherein the inspection is performed on one level of the wafer, the method further comprising identifying the criticality of a defect on the wafer based on the criticality of the critical portion in which the defect is located and data representative of at least one layer of the water above or below the one level.

31. The method of claim 30, further comprising generating a three-dimensional representation of the defect, the one level, and the at least one layer of the wafer.

32. A computer-implemented method, comprising determining one or more parameters for wafer defect review based on criticality associated with different areas of the water, wherein said determining is performed using a computer processor.

33. The method of claim 32, further comprising selecting the one or more parameters such that only defects located in critical portions of the wafer are reviewed.

34. The method of claim 33, wherein the one or more parameters are different for one or more of the critical portions.

35. The method of claim 32, further comprising sending information about the criticality to a tool configured to perform the wafer defect review.

36. A computer-implemented method, comprising determining one or more parameters for wafer defect analysis based on criticality associated with different areas of the wafer, wherein said determining is performed using a computer processor.

37. The method of claim 36, further comprising selecting the one or more parameters such that only defects located in critical portions of the wafer are analyzed.

38. The method of claim 37, wherein the one or more parameters are different for one or more of the critical portions.

39. The method of claim 36, further comprising sending information about the criticality to a tool configured to perform the wafer defect analysis.

* * * * *